(12) United States Patent
Hallahan et al.

(10) Patent No.: US 10,066,008 B2
(45) Date of Patent: Sep. 4, 2018

(54) MONOCLONAL ANTIBODIES TO HUMAN 14-3-3 EPSILON AND HUMAN 14-3-3 EPSILON SV

(71) Applicant: Washington University, St. Louis, MO (US)

(72) Inventors: Dennis E. Hallahan, St. Louis, MO (US); Heping Yan, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 50 days.

(21) Appl. No.: 15/054,691

(22) Filed: Feb. 26, 2016

(65) Prior Publication Data
US 2016/0194388 A1 Jul. 7, 2016

Related U.S. Application Data

(63) Continuation-in-part of application No. PCT/US2014/053207, filed on Aug. 28, 2014.

(60) Provisional application No. 61/907,677, filed on Nov. 22, 2013, provisional application No. 61/871,115, filed on Aug. 28, 2013.

(51) Int. Cl.
| | |
|---|---|
| *A61K 39/395* | (2006.01) |
| *C07K 16/18* | (2006.01) |
| *A61N 5/10* | (2006.01) |
| *C07K 16/30* | (2006.01) |
| *G01N 33/574* | (2006.01) |
| *A61K 49/00* | (2006.01) |
| *A61K 47/48* | (2006.01) |
| *A61K 51/10* | (2006.01) |

(52) U.S. Cl.
CPC ........ *C07K 16/18* (2013.01); *A61K 47/48569* (2013.01); *A61K 49/0058* (2013.01); *A61K 51/1045* (2013.01); *A61N 5/10* (2013.01); *C07K 16/30* (2013.01); *C07K 16/3023* (2013.01); *G01N 33/57423* (2013.01); *A61N 2005/1098* (2013.01); *C07K 2317/34* (2013.01); *C07K 2317/51* (2013.01); *C07K 2317/515* (2013.01); *C07K 2317/565* (2013.01); *C07K 2317/567* (2013.01)

(58) Field of Classification Search
None
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 5,585,089 A | 12/1996 | Queen et al. | |
| 2012/0093819 A1 | 4/2012 | Tremblay et al. | |

FOREIGN PATENT DOCUMENTS

| | | |
|---|---|---|
| WO | 2009067820 A1 | 6/2009 |
| WO | 2015031645 A1 | 3/2015 |

OTHER PUBLICATIONS

Rudikoff et al. (Proc Natl Acad Sci USA 1982 vol. 79 p. 1979) (Year: 1979).*
MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
Zhang, Q. et al., "High and Low Doses of Ionizing Radiation Induce Different Secretome Profiles in a Human Skin Model," PLOS ONE, Mar. 2014, pp. 1-8, vol. 9, No. 3, e92332.
Zuo, S. et al., "14-3-3 Epsilon Dynamically Interacts with Key Components of Mitogen-Activated Protein Kinase Signal Module for Selective Modulation of the TNF-alpha-Induced Time Course-Dependent NF-kB Activity," J. Proteome Res., 2010, pp. 3465-3478, vol. 9, American Chemical Society.
Albini, A. et al., "Growth by Interferon-Producing Cells: A Gene Therapy Approach," Am. J. Pathol., Apr. 2000, pp. 1381-1393, vol. 156, No. 4.
Aristizabal-Corrales, D. et al., "The 14-3-3 gene par-5 is required for germline development and DNA damage response in Caenorhabditis elegans," J. Cell Sci., Nov. 17, 2011, pp. 1716-1726, vol. 125.
Cai, W. et al., "In vitro and in vivo Characterization of 64Cu-Labeled Abegrin™, a Humanized Monoclonal Antibody against Integrin AlphavBeta3," Cancer Res., Oct. 1, 2006, pp. 9673-9681, vol. 66, No. 19.
Carpizo, D. et al., "Endogenous regulators of angiogenesis—emphasis on proteins with thrombospondin—type I motifs," Cancer and Metastasis Rev., 2000, pp. 159-165, vol. 19.
Chothia, C. et al., "Conformations of immunoglobulin hypervariable regions," Nature, Dec. 21-28, 1989, pp. 877-883, vol. 342, No. 6252.

(Continued)

*Primary Examiner* — Laura B Goddard
*Assistant Examiner* — Meera Natarajan
(74) *Attorney, Agent, or Firm* — Polsinelli PC

(57) ABSTRACT

The present invention provides isolated antibodies that bind to 14-3-3 epsilon that are useful in the recognition of tumor cells and tumor specific delivery of drugs and therapies.

17 Claims, 20 Drawing Sheets
(19 of 20 Drawing Sheet(s) Filed in Color)
Specification includes a Sequence Listing.

(56) References Cited

OTHER PUBLICATIONS

Clapp, C. et al., "The 16-Kilodalton N-Terminal Fragment of Human Prolactin Is a Potent Inhibitor of Angiogenesis," Endocrinology, Sep. 1993, pp. 1292-1299, vol. 133, No. 3.
Clynes, R. et al., "Fc receptors are required in passive and active immunity to melanoma," PNAS, Jan. 20, 1998, pp. 352-656, vol. 95, No. 2.
Clynes, R. et al., "Inhibitory Fc receptors modulate in vivo cytotoxicity against tumor targets," Nat. Med., Apr. 2000, pp. 443-446, vol. 6, No. 4.
Co, M. et al., "Humanized antibodies for antiviral therapy," PNAS, Apr. 1991, pp. 2869-2873, vol. 88, No. 7.
Dameron, K. et al., "The p53 Tumor Suppressor Gene Inhibits Angiogenesis by Stimulating the Production of Thrombospondin," Cold Spring Harbor Symposia on Quantitative Biology, 1994, pp. 483-489, vol. LIX.
Desjarlais, J. et al., "Optimizing engagement of the immune system by anti-tumor antibodies: an engineer's perspective," Drug Discovery Today, Nov. 2007, pp. 898-910, vol. 12, Nos. 21-22.
Divgi, C. et al., "Phase I/II Radioimmunotherapy Trial with Iodine-131-labeled Monoclonal Antibody G250 in Metastatic Renal Cell Carcinoma," Clin. Cancer Res., Nov. 1998, pp. 2729-2739, vol. 4, No. 11.
Eijan, A. et al., "Modulation of tumor-induced angiogenesis by proteins of extracellular matrix," Mol. Biother., Mar. 1991, pp. 38-40, vol. 3, No. 1.
Hariri, G. et al., "Radiation-Guided P-Selectin Antibody Targeted to Lung Cancer," Annals of Biomedical Engineering, May 2008, pp. 821-830, vol. 36, No. 5.
Hallahan, D. et al., "Radiation-Mediated Control of Drug Delivery," Am. J. Clin. Oncol., 2001, pp. 473-480, vol. 24, No. 5, Lippincott Williams & Wilkins, Inc., Philadelphia.
Hallahan, D. et al., "Targeting drug delivery to radiation-induced neoantigens in tumor microvasculature," J. Controlled Release, Jul. 6, 2001, pp. 183-191, vol. 74, Elsevier.
Ichikawa, A. et al., "Molecular analysis of cross-reactive human monoclonal antibody AE6F4 generated by in vitro immunization: Epitope mapping of AE6F4 antibody on 14-3-3 family proteins and cytokeratin 8," Cytotechnology, Jul. 2001, pp. 101-107, vol. 36.
Ingber, D. et al., "Synthetic analogues of fumagillin that inhibit angiogenesis and suppress tumour growth," Nature, Dec. 6, 1990, pp. 555-557, vol. 348.
International Search Report and Written Opinion dated Nov. 20, 2014 from related International Patent Application No. PCT/US2014/053207; 10 pgs.
Jarillo, J. et al., "Two related low-temperature-inducible genes of *Arabidopsis* encode proteins showing high homology to 14-3-3 proteins, a family of putative kinase regulators," Plant Molecular Biology, 1994, pp. 693-704, vol. 25, Kluwer Academic Publishers, Belgium.
Kabat, "Sequences of Proteins of Immunological Interest," National Institutes of Health, 1987 and 1991 [BOOK].
Kirk, C. et al., "Gene-Modified Dendritic Cells for Use in Tumor Vaccines," Human Gene Therapy, Apr. 10, 2000, pp. 797-806, vol. 11, Mary Ann Liebert, Inc.
Kolb, H. et al., "Click Chemistry: Diverse Chemical Function from a Few Good Reactions," Angew. Chem. Int. Ed., Jun. 1, 2001, pp. 2004-2021, vol. 40, No. 11, Wiley-VCH Verlag GmbH, Weinheim.
Kosfeld, M. et al., "Identification of a New Cell Adhesion Motif in Two Homologous Peptides from the COOH-terminal Cell Binding Domain of Human Thrombospondin," J. Biol. Chem., Apr. 25, 1993, pp. 8808-8814, vol. 268, No. 12.
Leal, M. et al., "Clinical implication of 14-3-3 epsilon expression in gastric cancer," World J. Gastroenterol., Apr. 7, 2012, pp. 1531-1537, vol. 18, No. 13, Baishideng.
Lee, E., et al., "14-3-3E protein increases matrix metalloproteinase-2 gene expression via p38 MAPK signaling in NIH3T3 fibroblast cells," Exp. Mol. Med., Jul. 2009, pp. 453-461, vol. 41, No. 7.
Leibel and Phillips, "Textbook of Radiation Oncology: Expert Consult," Third Edition [BOOK].
Lohse, J. et al., "Fluorescein-Conjugated Lysine Monomers for Solid Phase Synthesis of Fluorescent Peptides and PNA Oligomers," Bioconjugate Chem., Jul.-Aug. 1997, pp. 503-509, vol. 8, No. 4.
MacKensen, A. et al., "Immunostimulatory Cytokines in Somatic Cells and Gene Therapy of Cancer," Cytokine & Growth Factor Rev., 1997, pp. 119-128, vol. 8, No. 2, Elsevier Science Ltd., Great Britain.
Maione, T. et al., "Inhibition of Angiogenesis by Recombinant Human Platelet Factor-4 and Related Peptides," Science, New Series, Jan. 5, 1990, pp. 77-79, vol. 247, No. 4938, American Association for the Advancement of Science.
Martin, H. et al., "Antibodies against the major brain isoforms of 14-3-3 protein: An antibody specific for the 4-acetylated aminoterminus of a protein," FEBS, Oct. 1993, pp. 296-303, vol. 331, No. 3.
Mernaugh, R. et al., "Production and characterization of mouse ureteric bud cell-specific rat hybridoma antibodies itilizing subtractive immunization and high-throughput screening," J. Immunological Methods, 2005, pp. 115-127, vol. 306, Elsevier.
Ning, Y. et al., "An alternative strategy for high throughput generation and characterization of monoclonal antibodies against human plasma proteins using fractionated native proteins as immunogens," Proteomics, 2006, pp. 438-448, vol. 6, Wiley-VCH Verlag GmbH & Co. KGaA, Weinheim.
O'Reilly, M. et al., "Endostatin: An Endogenous Inhibitor of Angiogenesis and Tumor Growth," Cell, Jan. 24, 1997, pp. 277-285, vol. 88, Cell Press.
O'Reilly, M. et al., "Angiostatin: A Novel Angiogenesis Inhibitor That Mediates the Suppression of Metastases by a Lewis Lung Carcinoma," Cell, Oct. 21, 1994, pp. 315-328, vol. 79, Cell Press.
Oriente, F. et al., "Protein Kinase C-alpha Regulates Insulin Action and Degradation by Interacting with Insulin Receptor Substrate-1 and 14-3-3E," J. Bio. Chem., Dec. 9, 2005, pp. 40642-40649, vol. 280, No. 49, U.S.A.
Qi, W. et al., "Reduction of 14-3-3 Proteins Correlates with Increased Sensitivity to Killing of Human Lung Cancer Cells by Ionizing Radiation," Radiation Research, Aug. 2003, pp. 217-223, vol. 160, No. 2, Radiation Research Society.
Qi, W. et al., "Isoform-Specific Expression of 14-3-3 Proteins in Human Lung Cancer Tissues," Int. J. Cancer, 2005, pp. 359-363, vol. 113, Wiley-Liss, Inc.
Remington's Pharmaceutical Sciences, Mack Publishing Co., Easton Pa., 18th Edition [BOOK].
Richman, C. et al., "High-Dose Radioimmunotherapy Combined with Fixed, Low-Dose Paclitaxel in Metastatic Prostate and Breast Cancer by Using a MUC-1 Monoclonal Antibody, m170, Linked to Indium-111/Yttrium-90 via a Cathespin Cleavable Linker with Cyclosporine to Prevent Human Anti-mouse Antibody," Clin. Cancer Res., Aug. 15, 2005, pp. 5920-5927, vol. 11, No. 16.
Sakamoto, N. et al., "Inhibition of Angiogenesis and Tumor Growth by a Synthetic Laminin Peptide, CDPGYIGSR-NH2," Cancer Res., Feb. 1, 1991, pp. 903-906, vol. 51.
Sleister, H. et al., "Subtractive immunization: a tool for the generation of discriminatory antibodies to proteins of similar sequence," J. Immunological Methods, 2002, pp. 213-220, vol. 261, Elsevier.
Tang, S. et al., "14-3-3E Mediates the Cell Fate Decision-Making Pathways in Response of Hepatocellular Carcinoma to Bleomycin-Induced DNA Damage," PLOS ONE, Mar. 2013, pp. 1-14, vol. 8, No. 3, e55268.
Telles, E et al., "A novel pocket in 14-3-3E is required to mediate specific complex formation with cdc25C and to inhibit cell cycle progression upon activation of checkpoint pathways," Exp. Cell Res., 2009, pp. 1448-1457, vol. 315, Elsevier.
Tolsma, S. et al., "Transformation of NIH/3T3 to Anchorage Independence by H-Ras Is Accompanied by Loss of Suppressor Activity," Exp. Cell Res., 1993, pp. 232-239, vol. 205, Academic Press, Inc.

(56) References Cited

OTHER PUBLICATIONS

Voest, E. et al., "Inhibition of Angiogenesis in Vivo by Interleukin 12," J. Natl. Cancer Inst., Apr. 19, 1995, pp. 581-586, vol. 87, No. 8.
Walther, W. et al., "Therapeutic Genes for Cancer Gene Therapy," Molecular Biotechnology, 1999, pp. 21-28, vol. 13, Humana Press Inc.
Wang, Z. et al., "The Prognostic Value of 14-3-3 Isoforms in Vulvar Squamous Cell Carcinoma Cases: 14-3-3Beta and E Are Independent Prognostic Factors for These Tumors," PLoS ONE, Sep. 2011, pp. 1-6, vol. 6, No. 9, e24843.
Woltering, E. et al., "Somatostatin Analogues Inhibit Angiogenesis in the Chick Chorioallantoic Membrane," J. Surg. Res., 1991, pp. 245-251, vol. 50, Academic Press, Inc.
Wong, J. et al., "A Phase I Radioimmunotherapy Trial Evaluating 90Yttrium-labeled Anti-Carcinoembryonic Antigen (CEA) Chimeric T84.66 in Patients with Metastatic CEA-producing Malignancies," Clin. Cancer Res., Oct. 2000, pp. 3855-3863, vol. 6.

* cited by examiner

```
         10         20         30         40         50         60
MDDREDLVYQ AKLAEQAERY DEMVESMKKV AGMDVELTVE ERNLLSVAYK NVIGARRASW 70         80         90        100        110        120
RIISSIEQKE ENKGGEDKLK MIREYRQMVE TELKLICCDI LDVLDKHLIP AANTGESKVF 130        140        150        160        170        180
YYKMKGDYHR YLAEFATGND RKEAAENSLV AYKAASDIAM TELPPTHPIR LGLALNFSVF 190        200        210        220        230        240
YYEILNSPDR ACRLAKAAFD DAIAELDTLS EESYKDSTLI MQLLRDNLTL WTSDMQGDGE

250
EQNKEALQDV EDENQ
```

FIG. 1

```
          10         20         30         40         50         60
MVESMKKVAG MDVELTVEER NLLSVAYKNV IGARRASWRI ISSIEQKEEN KGGEDKLKMI 70         80         90        100        110        120
REYRQMVETE LKLICCDILD VLDKHLIPAA NTGESKVFYY KMKGDYHRYL AEFATGNDRK 130        140        150        160        170        180
EAAENSLVAY KAASDIAMTE LPPTHPIRLG LALNFSVFYY EILNSPDRAC RLAKAAFDDA 190        200        210        220        230
IAELDTLSEE SYKDSTLIMQ LLRDNLTLWT SDMQGDGEEQ NKEALQDVED ENQ
```

FIG. 2

H23 3Gyx3

H23 0Gy

Lanes. 1. H23 sham 0Gy   2. H23 3Gyx1   3. H23 3Gyx3

H23 cells 3Gyx3

H23 cells sham 0Gy

3Gyx3+7D4

5Gyx1+7D4

48 hour 96 hour 240 hour

0Gy+7D4

48 hour 96 hour 240 hour

5Gyx1+Ctrl-Ab

US 10,066,008 B2

MONOCLONAL ANTIBODIES TO HUMAN 14-3-3 EPSILON AND HUMAN 14-3-3 EPSILON SV

CROSS REFERENCE TO RELATED APPLICATIONS

This application claims the benefit of PCT application number PCT/US2014/053207, filed Aug. 28, 2014, which claims the benefit of U.S. provisional application No. 61/871,115, filed Aug. 28, 2013, and U.S. provisional application No. 61/907,677, filed Nov. 22, 2013, each of the disclosures of which are hereby incorporated by reference in their entirety.

GOVERNMENT SUPPORT

This invention was made with government support under 5R01 CA125757-06 awarded by the NIH. The government has certain rights in the invention.

FIELD OF THE INVENTION

The invention encompasses antibodies useful in the recognition of tumor cells and tumor specific delivery of drugs and therapies.

BACKGROUND OF THE INVENTION 14-3-3 proteins are a group of highly conserved proteins that are involved in many vital cellular processes such as metabolism, protein trafficking, signal transduction, apoptosis and cell cycle regulation. 14-3-3 proteins are phospho-serine/phospho-threonine binding proteins that have a diverse array of partners including transcription factors, biosynthetic enzymes, cytoskeletal proteins, signaling molecules, apoptosis factors and tumor suppressors. The 14-3-3 family consists of 7 isoforms; beta, gamma, epsilon, sigma, zeta, tau and eta. 14-3-3 proteins are ubiquitously expressed and self-assemble into homo- and heterodimers, with the exception of 14-3-3 sigma, which exclusively forms homodimers and is found in cells of epithelial origin only. Each monomer contains an independent ligand-binding site, thus the 14-3-3 dimer can interact with two target proteins simultaneously. 14-3-3 proteins are highly rigid structures and ligand binding can induce conformational changes that alter the stability and/or catalytic activity of the ligand. Furthermore, 14-3-3 protein binding can physically occlude sequence-specific or structural motifs on the target that prevent molecular interactions and/or modulate the accessibility of a target protein to modifying enzymes such as kinases, phosphatases and proteases. In addition, 14-3-3 proteins can act as a scaffold molecule to anchor target proteins within close proximity of one another. 14-3-3 proteins represent an integration point for proliferative, survival, apoptotic and stress signalling pathways. Members of the 14-3-3 protein family enhance the activity of many proteins with proliferative and/or survival functions, such as Raf kinases, and antagonize the activity of proteins that promote cell death and senescence, such as Bad, Bim and Bax. Because many 14-3-3 interactions are phosphorylation dependent, 14-3-3 proteins have been integrated into the core regulatory pathways that are crucial for normal growth and development. 14-3-3 proteins are directly involved in cellular processes such as cytokinesis, cell-contact inhibition, anchorage-independent growth and cell adhesion, and it is these pathways that often become dysregulated in disease states such as cancer.

Exposure of tumor cells to ionizing radiation (IR) is widely known to induce a number of cellular changes. One way that IR can affect tumor cells is through the development of neoantigens which are new molecules that tumor cells express at the cell membrane following some insult or change to the cell. There have been numerous reports in the literature of changes in both tumor and tumor vasculature cell surface molecule expression following treatment with IR. The usefulness of neoantigens for imaging and therapeutic applications lies in the fact that they are differentially expressed on the surface of irradiated tumor cells to a greater extent than on normal tissues. This differential expression provides a mechanism by which tumor cells can be "marked" by radiation for further targeting. Drug delivery vehicles or imaging agents conjugated to ligands that recognize and interact with the neoantigens can help to improve tumor-specific targeting and reduce systemic toxicity with cancer drugs.

SUMMARY OF THE INVENTION

In an aspect, the present invention encompasses cell line that expresses an antibody comprising an amino acid sequence selected from the group consisting of SEQ ID NO:3 and SEQ ID NO:4, wherein the antibody specifically binds 14-3-3 epsilon.

In another aspect, the present invention encompasses an isolated antibody that specifically binds 14-3-3 epsilon and comprises a light chain CDR3 comprising the amino acid sequence of SEQ ID NO:7 with zero to two amino acid substitutions.

In still another aspect, the present invention encompasses an isolated antibody that specifically binds 14-3-3 epsilon and comprises a heavy chain CDR3 comprising the amino acid sequence of SEQ ID NO:10 with zero to two amino acid substitutions.

In yet still another aspect, the present invention encompasses a method of detecting a tumor in a subject. The method comprises exposing a target area of the subject where the presence of a tumor is suspected to ionizing radiation; administering to the subject a composition to detect the presence of 14-3-3 epsilon in the target area, wherein the composition comprises one or more targeting antibodies, wherein each targeting antibody specifically binds to 14-3-3 epsilon exposed on an irradiated cell and is conjugated to a detectable label; and detecting the detectable label to detect the presence of 14-3-3 epsilon, wherein the presence of 14-3-3 epsilon indicates the presence of a tumor in the target area of the subject.

In a different aspect, the present invention encompasses a method of enhancing radiotherapy in a subject. The method comprises administering a pharmacologically effective amount of an isolated anti-14-3-3 epsilon antibody of claim 7 or claim 9 to the subject, such that radiotherapy is enhanced.

In other aspects, the present invention encompasses a method of delivering a therapeutic agent to a cell expressing 14-3-3 epsilon in a subject. The method comprises exposing a target area of the subject where the presence of a tumor is suspected to ionizing radiation; and administering an isolated anti-14-3-3 epsilon antibody of claim 7 or claim 9 to the subject.

In still other aspects, the present invention encompasses a method of detecting 14-3-3 epsilon in a sample. The method comprises obtaining a sample, and detecting and/or measuring the amount of 14-3-3 epsilon in the sample using an antibody of the invention.

BRIEF DESCRIPTION OF THE FIGURES

The application file contains at least one photograph executed in color. Copies of this patent application publication with color photographs will be provided by the Office upon request and payment of the necessary fee.

FIG. 1 shows the amino acid sequence of human 14-3-3 epsilon isoform 1 (SEQ ID NO:11). The underlined sequence identifies the binding epitope of antibody 7D4.

FIG. 2 shows the amino acid sequence of human 14-3-3 epsilon isoform SV (SEQ ID NO:12). The underlined sequence identifies the binding epitope of antibody 7D4.

(FIG. 4A) Colon, liver, lung, pancreas, (FIG. 4B) kidney and tongue tissue was evaluated. The 7D4 mouse monoclonal antibody to 14-3-3 epsilon showed no binding to colon, liver, pancreas, kidney or tongue. There was minimal binding to the lung.

FIG. 6A shows examples of phagocytic events (accumulation of red signal within mDCs; extension of pseudopodia; adhesion of mDCs to H23 cells). FIG. 6B and FIG. 6C controls show minimal phagocytic events. FIG. 6D shows a graph depicting the results of counting 50 random high-power fields to tally the number of phagocytic events.

FIG. 7A shows the production of interferon-gamma in cells treated with dendritic cells. Group 1: A, B, C, well 1-6; Group 2: D, E, F, well 1-6; Group 3: G, H, well 1-6 & A 7-12; Group 4: B, C, D, well 7-12; Group 5: E, F, well 7-12. FIG. 7B shows the quantification of interferon production. Group 1: 3Gyx3+7D4+mouse DC; Group 2: 3Gyx3+7D4+0; Group 3: 3Gyx3+NMIgG+MDC; Group 4: 0Gy+7D4+MDC; Group 5: 0Gy+0+0.

DETAILED DESCRIPTION

Figure 3A:
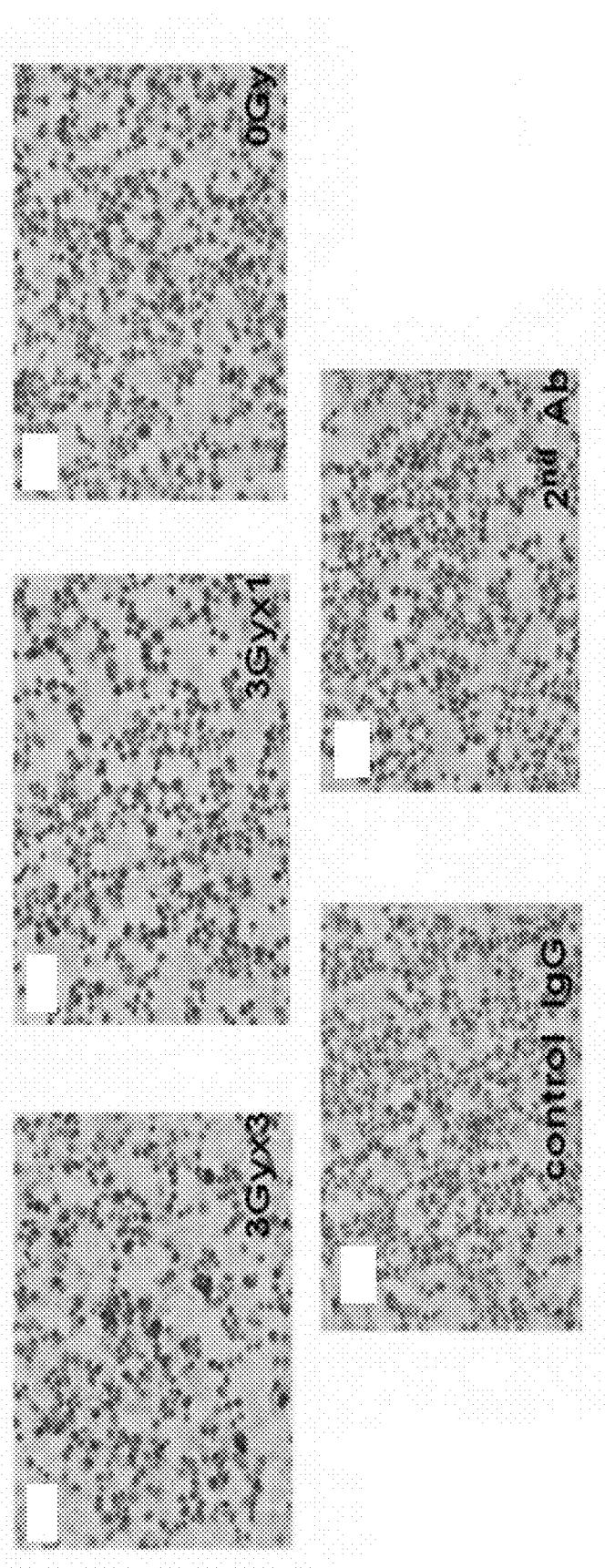
FIG. 3A depicts IHC results showing that the commercial anti 14-3-3 epsilon antibody strongly reacted with 3Gyx3 treated H23 lung cancer cells as well as 3Gyx1. The intensity in 3Gyx1 was much lower than 3Gyx3 treated H23 cells. Additionally, sham 0Gy treated H23 still had intense staining on tumor cells. Controls included normal rabbit IgG and second antibody.

The present invention provides antibodies that specifically bind 14-3-3 epsilon. Advantageously, these antibodies specifically bind to epitopes exposed on irradiated tumor cells and not normal cells. More specifically, these antibodies specifically bind to epitopes exposed on irradiated human lung cancer cells. The antibodies may be used to provide tumor specific delivery, for instance, of drugs or therapeutic agents, as well as enhancing the efficacy of radiotherapy.

As used herein, the term "14-3-3 epsilon" refers to human 14-3-3 epsilon and to orthologs from others species. Such orthologs are known in the art and include, but are not limited to the following NCBI Reference Sequences: XP_515815.4 (Pan troglodytes), NP_033562.3 (*Mus musculus*), NP_113791.1 (*Rattus norvegicus*), NP_776916.1 (*Bos taurus*), XP_854358.1 (*Canis familiaris*), NP_001006219.1 (*Gallus gallus*), BC045025.1 (*Xenopus laevis*), ECU89595.1 (*Xenopus tropicalis*), BC045325.1 (*Danio rerio*), AY370883.1 (*Oncorhynchus mykiss*), AB037679.1 (*Ciona intestinalis*), NP_732309.1 (*Drosophila melanogaster*), XP_322009.2 (*Anopheles gambiae*), NP_010384.1 (*Saccharomyces cerevisiae*), NP_594167.1 (*Schizosaccharomyces pombe*), NP_564451.2 (*Arabidopsis thaliana*), CF51152.1 (*Vitis vinifera*), AJ276594.1 (*Oryza sativa*), Y14200.1 (*Hordeum vulgare*), AY110486.1 (*Zea mays*), and AF548740.1 (*Triticum aestivum*). Further, the term "14-3-3 epsilon" encompasses all 14-3-3 epsilon splice variants. For example, human 14-3-3 epsilon is encoded by the gene YWHAE (Entrez Gene ID 7531). Alternative splicing produces two isoforms—isoform 1 (SEQ ID NO:11) and isoform SV (SEQ ID NO:12).

In an aspect, anti-14-3-3 epsilon antibodies of the invention may be used to detect 14-3-3 epsilon in vitro or in vivo. In another aspect, anti-14-3-3 epsilon antibodies useful herein also include antibodies that bind to specific regions of 14-3-3 epsilon, isoforms of 14-3-3 epsilon and to other forms of 14-3-3 epsilon. Specific regions of 14-3-3 epsilon include, but are not limited to, the C-terminal, the N-terminal, and other central domains. Isoforms of 14-3-3 epsilon include 14-3-3 epsilon isoform 1 (SEQ ID NO:11) and 14-3-3 epsilon isoform SV (SEQ ID NO:12), as well as splice variants from other species. Other forms of 14-3-3 epsilon include but are not limited to truncated, modified, soluble, insoluble, intracellular, extracellular, and dimerized or otherwise oligomerized forms, as well as 14-3-3 epsilon complexed with other proteins or molecules.

In another aspect, anti-14-3-3 epsilon antibodies useful herein include those which are isolated, characterized, purified, functional and have been recovered (obtained) from a process for their preparation and thus available for use herein in a useful form in an amount sufficient for conjugation to a drug, drug delivery vehicles or imaging agent.

In another aspect, antibodies useful herein include those antibodies which have been isolated, characterized, purified, are functional and have been recovered (obtained) from a process for their preparation and thus available for use herein in a useful form in an amount sufficient for an assay to detect and measure the amount of 14-3-3 epsilon in a biological sample.

In another aspect, anti-14-3-3 epsilon antibodies useful herein include those which are isolated, characterized, purified, functional and have been recovered (obtained) from a process for their preparation and thus available for use herein in a useful form in a therapeutically and medicinally sufficient amount.

The antibodies and methods of their use are described in further detail below.

I. Anti-14-3-3 Epsilon Antibodies

In an aspect, anti-14-3-3 epsilon antibodies useful herein include all antibodies that specifically bind an epitope within 14-3-3 epsilon. Generally speaking, the epitope is detectable on the surface of a tumor cell following irradiation. The epitope may or may not be detectable on the cell surface in the absence of irradiation. Alternatively, an epitope may be detectable on the surface of a tumor cell both in the absence of irradiation and following irradiation, though the detectable signal is greater following irradiation. In a specific embodiment, the epitope is selected from the group consisting of SEQ ID NO:13, SEQ ID NO:14 and SEQ ID NO:15.

The term "antibody' includes the term "monoclonal antibody." "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. The term "antibody" also includes bispecific monoclonal antibodies (i.e. a protein that comprises fragments of two different monoclonal antibodies and consequently binds two different antigens). A specific example of a bispecific monoclonal antibody may be a Bi-specific T-cell engager (BiTE) which is a fusion protein consisting of two single-chain variable fragments (scFvs) of different antibodies. In certain embodiments, BiTEs from a link between T cells and tumor cells. Accordingly, one scFv is a specific for 14-3-3 epsilon and one scFv binds a T cell. Additionally, an antibody of the invention may be a chimeric antigen receptor (CAR), also referred to as an artificial T cell receptor, a chimeric T cell receptor, or a chimeric immunoreceptor. CARs are engineered receptors, which graft an arbitrary specificity onto an immune effector cell. Typically, these receptors are used to graft the specificity of a monoclonal antibody onto a T cell. Also included within the definition "antibody" for example are single chain forms, generally designated Fv, regions, of antibodies with this specificity. These scFvs are comprised of the heavy and light chain variable regions connected by a linker. Methods of making and using scFvs are known in the art. Additionally, included within the definition "antibody" are single-domain antibodies, generally designated sdAb, which is an antibody fragment consisting of a single monomeric variable antibody domain. A sdAb antibody may be derived from camelids ($V_H$H fragments) or cartilaginous fishes ($V_{NAR}$ fragments). As long as the protein retains the ability specifically to bind its intended target, it is included within the term "antibody."

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

The basic antibody structural unit of an antibody useful herein comprises a tetramer. Each tetramer is composed of two identical pairs of polypeptide chains, each pair having one 'light' (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgO, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites. The chains exhibit the same general structure of relatively conserved framework regions (FR) joined by three hypervariable regions, also called complementarity determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-14-3-3 epsilon antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the 14-3-3 epsilon protein coding sequence or an appropriate subregion thereof. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-14-3-3 epsilon antibody that is composed partially or fully of amino acid sequence sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for 14-3-3 epsilon is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-14-3-3 epsilon antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, ct al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

In all instances, an antibody of the invention specifically binds 14-3-3 epsilon. In exemplary embodiments, an antibody of the invention specifically binds to human 14-3-3 epsilon isoform 1 (SEQ ID NO:11), human 14-3-3 epsilon isoform SV (SEQ ID NO:12), or human 14-3-3 epsilon isoform 1 and human 14-3-3 epsilon isoform SV. In other exemplary embodiments, an antibody of the invention specifically binds to an epitope on human 14-3-3 epsilon selected from the group consisting of SEQ ID NO:13, SEQ ID NO:14 and SEQ ID NO:15. The phrase "specifically binds" herein means antibodies bind to the protein with an affinity constant or Affinity of interaction (KD) in the range of at least 0.1 mM to 1 pM, or in the range of at least 0.1 pM to 10 nM, with a preferred range being 0.1 pM to 1 nM. The sequence of 14-3-3 epsilon from a variety of species is known in the art, and methods of determining whether an antibody binds to 14-3-3 epsilon are known in the art.

The antibodies of the present invention may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present invention are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

The antibodies of the present invention, including scFVs, may also be conjugated to a payload, such as a therapeutic agent, a detectable, and/or a delivery device (including, but not limited to, a liposome or a nanoparticle) containing the drug or detectable label. Methods of conjugating an antibody to a therapeutic agent, a detectable label, a liposome, a nanoparticle or other delivery device are known in the art. Generally speaking, the conjugation should not interfere with the antibody recognizing its target, and should not interfere with the active site of the target. In some instances, an antibody may be generated with a cleavable linkage between the antibody and the payload. Such a linker may allow release of the payload at a specific cellular location. Suitable linkers include, but are not limited to, amino acid chains and alkyl chains functionalized with reactive groups for conjugating to both the antibody of the invention and the detectable label and/or therapeutic agent. The therapeutic agent, detectable label, and delivery device are described in further detail below.

In an aspect, the present invention encompasses a cell line, the cell line expressing an antibody comprising an amino acid sequence selected from the group consisting of SEQ ID NO:3 and SEQ ID NO:4, wherein the antibody specifically binds 14-3-3 epsilon. In another embodiment, the present invention encompasses a cell line, the cell line expressing an antibody encoded by a nucleic acid sequence comprising a nucleic acid sequence selected from the group consisting of SEQ ID NO:1 and SEQ ID NO:2, wherein the antibody specifically binds 14-3-3 epsilon. In some embodiments, the cell line is an immortalized cell line. In preferred embodiments, the cell line is a hybridoma. Methods of generating hybridomas capable of producing antibodies are known in the art A preferred antibody is a humanized form of mouse antibody derived from a hybridoma designated 7D4. As used herein, the term "derived from" means that the "derived" antibody comprises at least one CDR region from the antibody produced by 7D4. Stated another way, the "derived antibody" comprises at least one CDR region comprised of the amino acid sequence selected from the group consisting of SEQ ID NO:5, 6, 7, 8, 9, and 10.

In one embodiment, an antibody of the invention may be derived from the hybridoma 7D4, and may be encoded by a nucleic acid sequence comprising 90, 91, 92, 93, 94, 95, 96, 97, 98, or 99% identity to the light chain variable region of SEQ ID NO:1, and/or may be encoded by a nucleic acid sequence comprising 90, 91, 92, 93, 94, 95, 96, 97, 98, or 99% identity to the heavy chain variable region of SEQ ID NO:2. In another embodiment, an antibody of the invention may be derived from the hybridoma 7D4, and may comprise an amino acid sequence with 90, 91, 92, 93, 94, 95, 96, 97, 98, or 99% identity to the light chain variable region of SEQ ID NO:3, and/or may comprise an amino acid sequence with 90, 91, 92, 93, 94, 95, 96, 97, 98, or 99% identity to the heavy chain variable region of SEQ ID NO:4. In each of the above embodiments, the antibody may be humanized.

In an exemplary embodiment of an antibody of the invention that binds to anti-14-3-3 epsilon, the antibody comprises the light chain nucleic acid sequence of SEQ ID NO:1 and the heavy chain nucleic acid sequence of SEQ ID NO:2 [i.e. the monoclonal antibody referred to herein as 7D4]. In another exemplary embodiment of an antibody of the invention that binds to anti-14-3-3 epsilon, the antibody comprises the light chain amino acid sequence of SEQ ID NO:3 and the heavy chain amino acid sequence of SEQ ID NO:4 [i.e. the monoclonal antibody referred to herein as 7D4].

In one embodiment, an antibody of the invention may comprise a light chain CDR1, such as antibody 1 of Table A. In another embodiment, an antibody of the invention may comprise a light chain CDR2, such as antibody 4 of Table A. In yet another embodiment, an antibody of the invention may comprise a light chain CDR3, such as antibody 6 of Table A. In an alternative embodiment, an antibody of the invention may comprise a combination of two or three light chain CDRs, such as the antibodies 2, 3 and 5 of Table A.

Similarly, in one embodiment, an antibody of the invention may comprise a heavy chain CDR1, such as antibody 7 of Table A. In another embodiment, an antibody of the invention may comprise a heavy chain CDR2, such as antibody 10 of Table A. In yet another embodiment, an antibody of the invention may comprise a heavy chain CDR3, such as antibody 12 of Table A. In an alternative embodiment, an antibody of the invention may comprise a combination of two or three heavy chain CDRs, such as the antibodies 8, 9 and 11 of Table A.

Alternatively, an antibody of the invention may comprise one or more light chain CDRs and one or more heavy chain CDRs, such as the antibodies 13-48 of Table A.

TABLE A

| Anti-body | Light Chain | | | Heavy Chain | | |
|---|---|---|---|---|---|---|
| | CDR1 | CDR2 | CDR3 | CDR1 | CDR2 | CDR3 |
| 1 | SEQ ID NO: 5 | | | | | |
| 2 | SEQ ID NO: 5 | SEQ ID NO: 6 | | | | |
| 3 | SEQ ID NO: 5 | SEQ ID NO: 6 | SEQ ID NO: 7 | | | |
| 4 | | SEQ ID NO: 6 | | | | |
| 5 | | SEQ ID NO: 6 | SEQ ID NO: 7 | | | |
| 6 | | | SEQ ID NO: 7 | | | |
| 7 | | | | SEQ ID NO: 8 | | |
| 8 | | | | SEQ ID NO: 8 | SEQ ID NO: 9 | |
| 9 | | | | SEQ ID NO: 8 | SEQ ID NO: 9 | SEQ ID NO: 10 |
| 10 | | | | | SEQ ID NO: 9 | |
| 11 | | | | | SEQ ID NO: 9 | SEQ ID NO: 10 |
| 12 | | | | | | SEQ ID NO: 10 |
| 13 | SEQ ID NO: 5 | | | SEQ ID NO: 8 | | |
| 14 | SEQ ID NO: 5 | | | SEQ ID NO: 8 | SEQ ID NO: 9 | |
| 15 | SEQ ID NO: 5 | | | SEQ ID NO: 8 | SEQ ID NO: 9 | SEQ ID NO: 10 |
| 16 | SEQ ID NO: 5 | | | | SEQ ID NO: 9 | |
| 17 | SEQ ID NO: 5 | | | | SEQ ID NO: 9 | SEQ ID NO: 10 |
| 18 | SEQ ID NO: 5 | | | | | SEQ ID NO: 10 |
| 19 | SEQ ID NO: 5 | SEQ ID NO: 6 | | SEQ ID NO: 8 | | |
| 20 | SEQ ID NO: 5 | SEQ ID NO: 6 | | SEQ ID NO: 8 | SEQ ID NO: 9 | |
| 21 | SEQ ID NO: 5 | SEQ ID NO: 6 | | SEQ ID NO: 8 | SEQ ID NO: 9 | SEQ ID NO: 10 |

TABLE A-continued

| Anti-body | Light Chain | | | Heavy Chain | | |
|---|---|---|---|---|---|---|
| | CDR1 | CDR2 | CDR3 | CDR1 | CDR2 | CDR3 |
| 22 | SEQ ID NO: 5 | SEQ ID NO: 6 | | | SEQ ID NO: 9 | |
| 23 | SEQ ID NO: 5 | SEQ ID NO: 6 | | | SEQ ID NO: 9 | SEQ ID NO: 10 |
| 24 | SEQ ID NO: 5 | SEQ ID NO: 6 | | | | SEQ ID NO: 10 |
| 25 | SEQ ID NO: 5 | SEQ ID NO: 6 | SEQ ID NO: 7 | SEQ ID NO: 8 | | |
| 26 | SEQ ID NO: 5 | SEQ ID NO: 6 | SEQ ID NO: 7 | SEQ ID NO: 8 | SEQ ID NO: 9 | |
| 27 | SEQ ID NO: 5 | SEQ ID NO: 6 | SEQ ID NO: 7 | SEQ ID NO: 8 | SEQ ID NO: 9 | SEQ ID NO: 10 |
| 28 | SEQ ID NO: 5 | SEQ ID NO: 6 | SEQ ID NO: 7 | | SEQ ID NO: 9 | |
| 29 | SEQ ID NO: 5 | SEQ ID NO: 6 | SEQ ID NO: 7 | | SEQ ID NO: 9 | SEQ ID NO: 10 |
| 30 | SEQ ID NO: 5 | SEQ ID NO: 6 | SEQ ID NO: 7 | | | SEQ ID NO: 10 |
| 31 | | SEQ ID NO: 6 | | SEQ ID NO: 8 | | |
| 32 | | SEQ ID NO: 6 | | SEQ ID NO: 8 | SEQ ID NO: 9 | |
| 33 | | SEQ ID NO: 6 | | SEQ ID NO: 8 | SEQ ID NO: 9 | SEQ ID NO: 10 |
| 34 | | SEQ ID NO: 6 | | | SEQ ID NO: 9 | |
| 35 | | SEQ ID NO: 6 | | | SEQ ID NO: 9 | SEQ ID NO: 10 |
| 36 | | SEQ ID NO: 6 | | | | SEQ ID NO: 10 |
| 37 | | SEQ ID NO: 6 | SEQ ID NO: 7 | SEQ ID NO: 8 | | |
| 38 | | SEQ ID NO: 6 | SEQ ID NO: 7 | SEQ ID NO: 8 | SEQ ID NO: 9 | |
| 39 | | SEQ ID NO: 6 | SEQ ID NO: 7 | SEQ ID NO: 8 | SEQ ID NO: 9 | SEQ ID NO: 10 |
| 40 | | SEQ ID NO: 6 | SEQ ID NO: 7 | | SEQ ID NO: 9 | |
| 41 | | SEQ ID NO: 6 | SEQ ID NO: 7 | | SEQ ID NO: 9 | SEQ ID NO: 10 |
| 42 | | SEQ ID NO: 6 | SEQ ID NO: 7 | | | SEQ ID NO: 10 |
| 43 | | | SEQ ID NO: 7 | SEQ ID NO: 8 | | |
| 44 | | | SEQ ID NO: 7 | SEQ ID NO: 8 | SEQ ID NO: 9 | |
| 45 | | | SEQ ID NO: 7 | SEQ ID NO: 8 | SEQ ID NO: 9 | SEQ ID NO: 10 |
| 46 | | | SEQ ID NO: 7 | | SEQ ID NO: 9 | |
| 47 | | | SEQ ID NO: 7 | | SEQ ID NO: 9 | SEQ ID NO: 10 |
| 48 | | | SEQ ID NO: 7 | | | SEQ ID NO: 10 |

In various embodiments, an antibody of the invention is humanized. For instance, in one embodiment, a humanized antibody of the invention may comprise a light chain variable region comprising a CDR1 of amino acid sequence SEQ ID NO:5 with zero to two amino acid substitutions, a CDR2 of amino acid sequence SEQ ID NO:6 with zero to two amino acid substitutions, and a CDR3 of amino acid sequence SEQ ID NO:7 with zero to two amino acid substitutions, and/or may comprise a heavy chain variable region comprising a CDR1 of amino acid sequence SEQ ID NO:8 with zero to two amino acid substitutions, a CDR2 of amino acid sequence SEQ ID NO:9 with zero to two amino acid substitutions, and a CDR3 of amino acid sequence SEQ ID NO:10 with zero to two amino acid substitutions. In a preferred embodiment, a humanized antibody of the invention may comprise a light chain variable region comprising a CDR1 of amino acid sequence SEQ ID NO:5 with zero to two amino acid substitutions, a CDR2 of amino acid sequence SEQ ID NO:6 with zero to two amino acid substitutions, a CDR3 of amino acid sequence SEQ ID NO:7 with zero to two amino acid substitutions, a heavy chain variable region comprising a CDR1 of amino acid sequence SEQ ID NO:8 with zero to two amino acid substitutions, a CDR2 of amino acid sequence SEQ ID NO:8 with zero to two amino acid substitutions, and a CDR3 of amino acid sequence SEQ ID NO:10 with zero to two amino acid substitutions. In an exemplary embodiment, a humanized antibody of the invention may comprise a light chain variable region comprising a CDR1 of amino acid sequence SEQ ID NO:5, a CDR2 of amino acid sequence SEQ ID NO:6, a CDR3 of amino acid sequence SEQ ID NO:7, a heavy chain variable region comprising a CDR1 of amino acid sequence SEQ ID NO:8, a CDR2 of amino acid sequence SEQ ID NO:9, and a CDR3 of amino acid sequence SEQ ID NO:10. The invention also encompasses the corresponding nucleic acid sequences of SEQ ID NO:5, 6, 7, 8, 9, and 10, which can readily be determined by one of skill in the art, and may be incorporated into a vector or other large DNA molecule, such as a chromosome, in order to express an antibody of the invention.

The invention also encompasses a vector comprising a nucleic acid sequence capable of encoding an antibody of the invention. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors. An expression vector encoding an antibody of the invention may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding an antibody of the invention that is introduced to the cell may be linear or circular, may be single-stranded or double-stranded, and may be DNA, RNA, or any modification or combination thereof. An expression vector encoding an antibody of the invention may be administered to a subject as gene therapy.

(a) Detectable Label

In an aspect, an antibody of the invention may be conjugated to a detectable label. A detectable label may be directly conjugated to an antibody of the invention or may be indirectly conjugated to an antibody of the invention. In an embodiment, a detectable label may be complexed with a chelating agent that is conjugated to an antibody of the invention. In another embodiment, a detectable label may be complexed with a chelating agent that is conjugated to a linker that is conjugated to an antibody of the invention. In still another embodiment, a detectable label may be conjugated to a linker that is conjugated to an antibody of the invention. In still yet another embodiment, a detectable label may be indirectly attached to an antibody of the invention by the ability of the label to be specifically bound by a second molecule. One example of this type of an indirectly attached label is a biotin label that can be specifically bound by the second molecule, streptavidin or other biotin binding protein. Single, dual or multiple labeling may be advantageous. An isolated antibody of the present invention may be conjugated to one, two, three, four, or five types of detectable labels.

As used herein, a "detectable label" is any type of label which, when attached to an antibody of the invention renders the antibody detectable. A detectable label may also be toxic to cells or cytotoxic. Accordingly, a detectable label may also be a therapeutic agent or cytotoxic agent. In general, detectable labels may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

A detectable label emits a signal that can be detected by a signal transducing machine. In some cases, the detectable label can emit a signal spontaneously, such as when the detectable label is a radionuclide. In other cases the detectable label emits a signal as a result of being stimulated by an external field such as when the detectable label is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) machines. As such, the detectable label comprises a label that can be detected using magnetic resonance imaging, scintigraphic imaging, ultrasound, or fluorescence. In a specific embodiment, the detectable label comprises a label that can be detected using positron emission tomography, single photon emission computed tomography, gamma camera imaging, or rectilinear scanning.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. $B_{12}$ or an analog thereof can be labeled for fluorescence detection by labeling the agent with a fluorophore using techniques well known in the art (see, e.g., Lohse et al., Bioconj Chem 8:503-509 (1997)). For example, many known dyes are capable of being coupled to $NH_2$-terminal groups. Alternatively, a fluorochrome such as fluorescein may be bound to a lysine residue of a peptide linker. In a specific embodiment, an alkyne modified dye, such an Alexa Fluor dye, may be clicked to an azido modified $B_{12}$ using, for example, Sharpless click chemistry (Kolb et al., Angew Chem Int Ed 2001; 40: 2004-2021, which incorporated by reference in its entirety).

A radionuclide may be a γ-emitting radionuclide, Auger-emitting radionuclide, β-emitting radionuclide, an α-emitting radionuclide, or a positron-emitting radionuclide. A radionuclide may be a detectable label and/or a therapeutic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97, 103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived there from. In a specific embodiment, a radionuclide is selected from the group consisting of copper-64, zirconium-89, yttrium-86, yttrium-90, technetium-99m, iodine-125, iodine-131, lutetium-177, rhenium-186 and rhenium-188.

A variety of metal atoms may be used as a detectable label. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms may be metal ions in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

In an embodiment where an antibody of the invention is conjugated to a non-radioactive isotope, it may be used in neutron capture therapy (NCT). Neutron capture therapy (NCT) is a noninvasive therapeutic modality for treating locally invasive malignant tumors. NCT is a two step procedure: first, the subject is injected with a tumor localizing drug containing a non-radioactive isotope that has a high propensity or cross section ($\sigma$) to capture slow neutrons. The cross section of the capture agent is many times greater than that of the other elements present in tissues such as hydrogen, oxygen, and nitrogen. In the second step, the subject is radiated with epithermal neutrons, which after losing energy as they penetrate tissue, are absorbed by the capture agent, which subsequently emits high-energy charged particles, thereby resulting in a biologically destructive nuclear reaction. In certain embodiments, the non-radioactive isotope may be boron-10 or gadolinium.

(b) Therapeutic Agent

In an aspect, an antibody of the invention may be conjugated to a therapeutic agent, such that the therapeutic agent can be selectively targeted to a cell expressing 14-3-3 epsilon. In a specific embodiment, the therapeutic agent can be selectively targeted to an irradiated tumor cell expressing 14-3-3 epsilon. The therapeutic agent may be directly conjugated to an antibody of the invention or may be indirectly conjugated to an antibody of the invention. In an embodiment, the therapeutic agent may be complexed with a chelating agent that is conjugated to an antibody of the invention. In another embodiment, the therapeutic agent may be complexed with a chelating agent that is conjugated to a linker that is conjugated to an antibody of the invention. In still another embodiment, the therapeutic agent may be conjugated to a linker that is conjugated to an antibody of the invention. In still yet another embodiment, the therapeutic agent may be conjugated to a linker that is conjugated to a chelating agent that is complexed with a detectable label and conjugated to an antibody of the invention.

A "therapeutic agent" is any compound known in the art that is used in the detection, diagnosis, or treatment of a condition or disease. Such compounds may be naturally-occurring, modified, or synthetic. Non-limiting examples of therapeutic agents may include drugs, therapeutic compounds, toxins, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Such therapeutic agents may be water soluble or may be hydrophobic. Non-limiting examples of therapeutic agents may include immune-related agents, thyroid agents, respiratory products, antineoplastic agents, anti-helmintics, anti-malarials, mitotic inhibitors, hormones, toxins, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, anti-biotics, anti-inflammatories, anti-rheumatics, narcotics, cardiac glycosides, neuromuscular blockers, sedatives, local anesthetics, general anesthetics, or radioactive atoms or ions. Non-limiting examples of therapeutic agents are described below. In a specific embodiment, a therapeutic agent may be a compound used in the detection diagnosis or treatment of cancer. The therapeutic agent preferably reduces or interferes with tumor growth or otherwise reduces the effect of the tumor within the body or organism. A therapeutic agent that reduces the symptoms produced by the tumor or reduces tumor growth is suitable for the present invention. Additionally, any therapeutic agent that reduces the symptoms associated with tumor cell growth will work for purposes of the present invention.

An antibody of the invention may be conjugated to one, two, three, four, or five therapeutic agents. A linker may or may not be used to conjugate a therapeutic agent to an antibody of the invention. Generally speaking, the conjugation should not interfere with the antibody binding to 14-3-3 epsilon. In some instances, an antibody of the invention may be generated with a cleavable linkage between the antibody and therapeutic agent. Such a linker may allow release of the therapeutic agent at a specific cellular location. In other instances, an antibody of the invention may be generated with an enzyme linked to it to create a prodrug. For example, cytidine deaminase may be linked to an antibody of the invention. The cytidine deaminase then cleaves the prodrug to create a cytotoxic drug.

A therapeutic agent of the invention may be a toxin. The term "toxin" means the toxic material or product of plants, animals, microorganisms (including, but not limited to, bacteria, viruses, fungi, rickettsiae or protozoa), or infectious substances, or a recombinant or synthesized molecule, whatever theft origin and method of production. A toxin may be a small molecule, peptide, or protein that is capable of causing disease on contact with or absorption by body tissues interacting with biological macromolecules such as enzymes or cellular receptors. A toxin may be a "biotoxin" which is used to explicitly identify the toxin as from biological origin. Biotoxins may be further classified into fungal biotoxins, or short mycotoxins, microbial biotoxins, plant biotoxins, short phytotoxins and animal biotoxins. Non-limiting examples of biotoxins include: endotoxins produced by bacteria, such as *Pseudomonas* endotoxin; cyanotoxins produced by cyanobacteria, such as microcystins, nodularins, anatoxin-a, cylindrospermopsins, lyngbya-toxin-a, saxitoxin, lipopolysaccharides, aplysiatoxins, BMAA; dinotoxins produced by dinoflagellates, such as saxitoxins and gonyautoxins; necrotoxins produced by, for example, the brown recluse or "fiddle back" spider, most rattlesnakes and vipers, the puff adder, *Streptococcus pyogenes*; neurotoxins produced by, for example, the black widow spider, most scorpions, the box jellyfish, elapid snakes, the cone snail, the Blue-ringed octopus, venomous fish, frogs, palythoa coral, various different types of algae, cyanobacteria and dinoflagellates, such as botulinum toxin (e.g. Botox), tetanus toxin, tetrodotoxin, chlorotoxin, conotoxin, anatoxin-a, bungarotoxin, caramboxin, curare; myotoxins, found in, for example, snake and lizard venoms; and cytotoxins such as ricin, from castor beans, apitoxin, from honey bees, and T−2 mycotoxin, from certain toxic mushrooms. In certain embodiments, a toxin is a cytotoxin. In an embodiment, a cytotoxin is an endotoxin from *Pseudomonas*.

A therapeutic agent of the invention may be a small molecule therapeutic, a therapeutic antibody, a therapeutic nucleic acid, or a chemotherapeutic agent. Non-limiting examples of therapeutic antibodies may include muromomab, abciximab, rituximab, daclizumab, basiliximab, palivizumab, infliximab, trastuzumab, etanercept, gemtuzumab, alemtuzumab, ibritomomab, adalimumab, alefacept, omalizumab, tositumomab, efalizumab, cetuximab, bevacizumab, natalizumab, ranibizumab, panitumumab, eculizumab, and certolizumab. A representative therapeutic nucleic acid may encode a polypeptide having an ability to induce an immune response and/or an anti-angiogenic response in vivo. Representative therapeutic proteins with immunostimulatory effects include but are not limited to cytokines (e.g., an interleukin (IL) such as IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein. Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991). Representative proteins with both immunostimulatory and anti-angiogenic activities may include IL12, interferon-γ, or a chemokine. Other therapeutic nucleic acids that may be useful for cancer therapy include but are not limited to nucleic acid sequences encoding tumor suppressor gene products/antigens, antimetabolites, suicide gene products, and combinations thereof.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. A cytotoxic agent is any naturally-occurring, modified, or synthetic compound that is toxic to tumor cells. Such agents are useful in the treatment of neoplasms, and in the treatment of other symptoms or diseases characterized by cell proliferation or a hyperactive cell population. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof. In an exemplary embodiment, the chemotherapeutic agent is selected from the group consisting of liposomal doxorubicin and nanoparticle albumin docetaxel.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites may include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcitabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non limiting examples of angiogeneisis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1 BB ligand, and Apo-1 ligand.

Non-limiting examples of photodynamic therapeutic agents may include aminolevulinic acid, methyl aminolevulinate, retinoids (alitretinon, tamibarotene, tretinoin), and temoporfin.

Other antineoplastic agents may include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The dose of the chemotherapeutic agent can and will vary depending upon the agent and the type of tumor or neoplasm. A skilled practitioner will be able to determine the appropriate dose of the chemotherapeutic agent.

Other therapeutic agents may comprise a virus or a viral genome such as an oncolytic virus. An oncolytic virus comprises a naturally occurring virus that is capable of killing a cell in the target tissue (for example, by lysis) when it enters such a cell.

(c) Delivery Vehicle

An antibody of the invention may be conjugated to a vehicle for cellular delivery. In these embodiments, typically an antibody of the invention, which may or may not be conjugated to a detectable label and/or therapeutic agent, is encapsulated in a suitable vehicle to either aid in the delivery of the compound to target cells, to increase the stability of the antibody, or to minimize potential toxicity of the antibody. As will be appreciated by a skilled artisan, a variety of vehicles are suitable for delivering an antibody of the present invention. Non-limiting examples of suitable structured fluid delivery systems may include nanoparticles, liposomes, microemulsions, micelles, dendrimers and other phospholipid-containing systems. Methods of incorporating antibodies into delivery vehicles are known in the art. Although various embodiments are presented below, it will be appreciate that other methods known in the art to incorporate an antibody of the invention into a delivery vehicle are contemplated.

In one alternative embodiment, a liposome delivery vehicle may be utilized. Liposomes, depending upon the embodiment, are suitable for delivery of the antibody of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the antibody of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the antibody of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied.

These parameters include, but are not limited to, temperature, pH, concentration of methionine compound, concentration and composition of lipid, concentration of multivalent cations, rate of mixing, presence of and concentration of solvent.

In another embodiment, an antibody of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The antibody of the invention may be encapsulated in a microemulsion by any method generally known in the art.

In yet another embodiment, an antibody of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of an dendrimer to facilitate absorption across the skin. Any of the phospholipids detailed for use in liposome embodiments are suitable for use in dendrimer embodiments. Any method generally known in the art may be utilized to make dendrimers and to encapsulate antibodies of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods of Using Anti-14-3-3 Epsilon Antibodies

In an aspect, the present invention provides anti-14-3-3 epsilon antibodies to detect 14-3-3 epsilon in vitro and/or in vivo. For example, anti-14-3-3 epsilon antibodies may be used to detect and measure the amount of 14-3-3 epsilon in a biological sample. Alternatively, anti-14-3-3 epsilon antibodies may be used to detect and measure the amount of 14-3-3 epsilon in a subject. In another aspect, the present invention provides anti-14-3-3 epsilon antibodies that can be used to provide tumor specific delivery, for instance, of drugs, therapeutic agents or imaging agents as well as enhancing the efficacy of radiotherapy. In still another aspect, the present invention provides anti-14-3-3 epsilon antibodies that can be used to detect a tumor in a subject.

(a) Methods to Detect and Measure the Amount of 14-3-3 Epsilon in a Biological Sample In an aspect, the invention provides means to detect 14-3-3 epsilon in a sample. In another aspect, the invention provides means to measure the amount of 14-3-3 epsilon in a sample. The method generally comprises (i) obtaining a sample from, and (ii) detecting and/or measuring the amount of 14-3-3 epsilon in the sample using an antibody that specifically binds 14-3-3 epsilon. Suitable antibodies are described above in Section I. The sample may be obtained from a subject (i.e. biological sample) or may be an immortalized cell line.

As used herein, the term "biological sample" refers to a sample obtained from a subject. Any biological sample containing 14-3-3 epsilon is suitable. Numerous types of biological samples are known in the art. Suitable biological sample may include, but are not limited to, tissue samples or bodily fluids. In some embodiments, the sample may be a bodily fluid comprising a cell expressing 14-3-3 epsilon on the cell surface. Non-limiting examples of suitable bodily fluids include blood, plasma, serum, lung aspirate, pleural fluid, and sputum. The fluid may be used "as is", the cellular components may be isolated from the fluid, or a protein fraction may be isolated from the fluid using standard techniques. In preferred embodiments, the biological sample is a tissue sample such as a tissue biopsy. The tissue biopsy may be a biopsy of tumor. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. The sample may also be primary and/or transformed cell cultures derived from tissue from the subject.

Suitable subjects include, but are not limited to, a human, a livestock animal, a companion animal, a lab animal, and a zoological animal. A subject may or may not be known to have a tumor comprising a cell expressing 14-3-3 epsilon on the cell surface. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that 14-3-3 epsilon can be accurately detected and the amount measured according to the invention.

Once a sample is obtained, it is processed in vitro to detect and measure the amount of 14-3-3 epsilon using an anti-14-3-3 epsilon antibody. All suitable methods for detecting and measuring an amount of protein using an antibody known to one of skill in the art are contemplated within the scope of the invention. Methods for detecting and measuring an amount of protein using an antibody (i.e. "antibody-based methods") are well known in the art. Non-limiting examples include an ELISA, a sandwich immunoassay, a radioimmunoassay, an immunoblot or Western blot, flow cytometry, immunohistochemistry, and an array.

In general, an antibody-based method of detecting and measuring an amount of 14-3-3 epsilon comprises contacting some of the sample, or all of the sample, comprising 14-3-3 epsilon with an anti-14-3-3 epsilon antibody under conditions effective to allow for formation of a complex between the antibody and the 14-3-3 epsilon protein. Typically, the entire sample is not needed, allowing one skilled in the art to repeatedly detect and measure the amount of 14-3-3 epsilon in the sample. The method may occur in solution, or the antibody or 14-3-3 epsilon protein comprising the sample may be immobilized on a solid surface. Non-limiting examples of suitable surfaces may include microtitre plates, test tubes, slides, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-14-3-3 epsilon antibody may also be attached to the substrate non-covalently. For example, a biotinylated anti-14-3-3 epsilon antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-14-3-3 epsilon antibody composition to the sample and incubating the mixture for a period of time long enough for the anti-14-3-3 epsilon antibody to bind to any antigen present. After this time, the complex will be washed and the complex may be detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories—competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry.

In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an anti-14-3-3 epsilon antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one an anti-14-3-3 epsilon antibody attached to the substrate is located at one or more spatially defined addresses of the array. For example, an array may comprise at least one, at least two, at least three, at least four, or at least five anti-14-3-3 epsilon antibodies, each antibody recognizing the same or different epitope 14-3-3 epsilon epitope, and each antibody may be may be at one, two, three, four, five, six, seven, eight, nine, ten or more spatially defined addresses.

(b) Tumor Specific Delivery

In another aspect, the present invention provides a method of delivering a therapeutic agent to a cell expressing 14-3-3 epsilon. Accordingly, an antibody of the present invention, as described in Section I, may be used in treating, stabilizing and preventing cancer and associated diseases in a subject. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. The inventors have shown that an antibody of the invention activates phagocytosis of cells bound by the antibody thereby reducing the amount of cancer cells expressing 14-3-3 epsilon. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of an antibody of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

An antibody of the present invention may be indirectly or directly coupled to radionuclides or chemotherapeutic agents as described above in order to provide specific delivery of radiation and chemotherapy to the site of a tumor. Further, the composition of the present invention may be part of a combination therapy. Preferably, a combination therapy would include the use of the antibody of the present invention along with a radiation therapy or chemotherapy course of treatment. It has also been suggested that antibody compositions, such as those described herein, may increase the susceptibility of tumor cells to the effects of chemotherapy or radiation. In preferred embodiments, the composition of the invention may be used to enhance the efficacy of cancer radiotherapy.

In yet another aspect, the present invention provides a method of detecting a tumor in a subject. The method comprises exposing a target area of the subject where the presence of a tumor is suspected to ionizing radiation, administering to the subject a composition to detect the presence of 14-3-3 epsilon in the target area, wherein the composition comprises one or more targeting antibodies, wherein each targeting antibody specifically binds to 14-3-3 epsilon exposed on an irradiated cell and is conjugated to a detectable label, and detecting the detectable label to detect the presence of 14-3-3 epsilon, wherein the presence of 14-3-3 epsilon indicates the presence of a tumor in the target area of the subject. In preferred embodiments, the method may be used to diagnose or image a cancer in a subject. In some embodiments, a method for detecting a tumor can comprise (a) exposing a suspected tumor to ionizing radiation; (b) biopsing a suspected tumor; (c) contacting an antibody of the invention with the suspected tumor in vitro; and (d) detecting the detectable label, whereby a tumor is diagnosed.

Binding may be detected using microscopy (fluorescent microscopy, confocal microscopy, or electron microscopy), magnetic resonance imaging (including MTI, MRS, DWI and fMRI), scintigraphic imaging (SPECT (Single Photon Emission Computed Tomography), PET (Positron Emission Tomography), gamma camera imaging, and rectilinear scanning), radiography, or ultrasound. The detectable label may be detectable in situ, in vivo, ex vivo, and in vitro.

The antibody compositions and subject are as described above. The cancer, the radiotherapy, and the administration of the compositions are described below.

An antibody of the invention may be used to treat or recognize a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In specific embodiments, the neoplasm or cancer is non-small cell lung carcinoma.

Suitable therapeutic agents for neoplasms and cancers are known in the art, and will depend upon the type and stage of cancer. Suitable therapeutic agents are described in Section I. Summaries of cancer drugs, including information regarding approved indications, may be found via the National Cancer Institute at the National Insitutes of Health (www.cancer.gov/cancertopics/druginfo/alphalist) and the FDA Approved Drug Product database (www.accessdata.fda.gov/scripts/cder/drugsatfda/). In a specific embodiment, the cancer is non-small cell lung carcinoma. Suitable therapeutics agents for the treatment of non-small cell lung carcinoma include, but are not limited to, EGFR inihbitors, VEGF inhibitors, tyrosine kinase inhibitors, and chemotherapeutics. Non-limiting examples of drugs approved for the treatment of NSCLC include methotrexate, Abraxane, Afatinib, Alimta, Avastin, Bevacizumab, Carboplatin, Cisplatin, Crizotinib, Erlotinib hydrochloride, Folex, Folex PFS, gefitinib, Gilotrif, Gemcitabine hydrochloride, Gemzar, Iressa, Methotrexate, Mexate, Mexate-AQ, Paclitaxel, Paclitaxel-albumin stabilized nanoparticle formulation, Paraplat, Paraplatin, Platinol, Tarceva, Taxol, and Xalkori.

In an aspect, the method comprises exposing a target area of a subject where the presence of a tumor is suspected to ionizing radiation. Low doses of radiation can be used for selective targeting using the antibody compositions disclosed herein. In some embodiments, the dose of radiation comprises up to about 2 Gy ionizing radiation. Higher radiation doses can also be used, especially in the case of local radiation treatment as described hereinbelow.

Radiation can be localized to a tumor using conformal irradiation, brachytherapy, or stereotactic irradiation. The threshold dose for inductive changes can thereby be exceeded in the target tissue but avoided in surrounding normal tissues. A "target tissue" as used herein refers to an intended site for accumulation of an antibody following administration to a subject. For example, the methods disclosed herein can employ a target tissue comprising an irradiated tumor. A "control tissue" as used herein refers to a site suspected to substantially lack binding and/or accumulation of an administered antibody. For example, in accordance with the methods of the presently disclosed subject matter, a non-irradiated tumor and a non-cancerous tissue are control tissues. In some embodiments, doses of at least about 2 Gy ionizing radiation can be used, and in some embodiments a dose of about 10 Gy to about 20 Gy ionizing radiation can be used. For treatment of a subject having two or more tumors, local irradiation enables differential drug administration and/or dose at each of the two or more tumors. Alternatively, whole body irradiation can be used, as permitted by the low doses of radiation required for targeting of antibodies disclosed herein. Radiotherapy methods suitable for use in the practice of the presently disclosed subject matter can be found in Leibel & Phillips, 1998, among other sources.

In an embodiment, the radiation treatment comprises administration of less than about 2 Gy ionizing radiation. In another embodiment, the radiation treatment comprises at least about 2 Gy ionizing radiation, in some embodiments about 2 Gy to about 3 Gy ionizing radiation, and in some embodiments about 2 Gy to about 6 Gy ionizing radiation. In other embodiments, radiation treatment comprises about 10 Gy to about 20 Gy ionizing radiation.

Administration of a composition to a subject can be performed by irradiating the tumor prior to, concurrent with, or subsequent to administration of a composition of the invention. Accordingly, the tumor is irradiated in some embodiments 0 hours to about 24 hours before administration of the composition, and in some embodiments about 4 hours to about 24 hours before administration of the composition.

In certain aspects, a pharmacologically effective amount of an antibody of the invention, including immunologically reactive fragments, may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living patient could be made up to contain 1 mL sterile buffered water of phosphate buffered saline and about 1-1000 mg of any one of or a combination of the humanized antibody of the present discovery. In a specific embodiment, the antibody composition may have 100-300 mg of antibody per administration. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-14-3-3 episilon antibody concentration. Therapeutic agents of the discovery can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antibody stability (chemical and physical) and comfort to the patient when administered. Generally, a pH between 4 and 8 is tolerated. Doses will vary from individual to individual based on size, weight, and other physiobiological characteristics of the individual receiving the successful administration.

For therapeutic applications, a therapeutically effective amount of a composition of the invention is administered to a subject. A "therapeutically effective amount" is an amount of the therapeutic composition sufficient to produce a measurable biological tumor response (e.g., an immunostimulatory, an anti-angiogenic response, a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about 0.01 mg/kg to about 100 mg/kg of an anti-14-3-3 epsilon antibody described herein. Doses can range from about 0.05 mg/kg to about 50 mg/kg, more preferably from about 0.1 mg/kg to about 25 mg/kg.

For diagnostic applications, a detectable amount of a composition of the invention is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled antibody prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of proteins such as antibodies, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

III. Kits

In another aspect, a kit is provided for use in diagnostic or therapeutic embodiments of the invention. The kit includes an antibody of the invention, and a detectable label, therapeutic agent, chelating agent, and/or a linker, as described in Section I. In an embodiment, each component of the kit (an antibody and a detectable label, therapeutic agent, chelating agent, and/or linker) is separately packaged in the kit. In another preferred embodiment, the kit includes a predetermined amount of the antibody and the detectable label, therapeutic agent, chelating agent, and/or linker (e.g., an amount sufficient for diagnosing or treating cancer in a subject). The antibody and the detectable label, therapeutic agent, chelating agent, and/or linker can be lyophilized to enable long-term storage. The antibody and detectable label, therapeutic agent, chelating agent, and/or linker may be sealed in a sterilized container. The kit preferably includes instructions for using the kit and its contents.

TABLE B

Sequence listings

| SEQ ID NO: | Description | SEQUENCE |
|---|---|---|
| 1 | Light chain: DNA sequence | GACATTGTGATGACACAGTCTCCATCCTCCCTGGCTATGTCAGTAGG ACAGAAGGTCACTATGAGCTGCAAGTCCAGTCAGAGCCTTTTAAATA GTAGCAATCAAAAGAACTATTTGGCCTGGTACCAGCAGAAACCAGGA CAGTCTCCTAAACTTCTGGTATACTTTGCATCCACTAGGGAATCTGG |

TABLE B-continued

Sequence listings

| SEQ ID NO: | Description | SEQUENCE |
|---|---|---|
|  |  | GGTCCCTGATCGCTTCATAGGCAGTGGATCTGGGACAGATTTCACTC TTACCATCAGCAGTGTGCAGGCTGAAGACCTGGCAGATTACTTCTGT CAGCAACATTATAGCACTCCGCTCACGTTCGGTGCTGGGACCAAGCT GGAGCTGAAA |
| 2 | Heavy chain: DNA sequence | CAGGTTCAGCTGCAGCAGTCTGGAGCTGAGCTGATGAAGCCTGGGGC CTCAGTGAAGATATCCTGCAAGGCTACTGGCTACACATTCAGTAGCT ACTGGATAGAGTGGGTAAAGCAGAGGCCTGGACATGGCCTTGAGTGG ATTGGAGAGATTTTACCTGGAAGTGGTAGTACTAACTACAATGAGAA GTTCAAGGGCAAGGCCACATTCACTGCAGATACATCCTCCAACACAG CCTACATGCAACTCAGCAGCCTGACATCTGAGGACTCTGCCGTCTAT TACTGTGCAAGATCGGTATGGTTACGACGTGATTTTGCTTACTGGGG CCAAGGGACTCTGGTCACTGTCTCTGCA |
| 3 | Light chain: AA sequence | DIVMTQSPSSLAMSVGQKVTMSCKSSQSLLNSSNQKNYLAWYQQKPG QSPKLLVYFASTRESGVPDRFIGSGSGTDFTLTISSVQAEDLADYFC QQHYSTPLTFGAGTKLELK |
| 4 | Heavy chain: AA sequence | QVQLQQSGAELMKPGASVKISCKATGYTFSSYWIEWVKQRPGHGLEW IGEILPGSGSTNYNEKFKGKATFTADTSSNTAYMQLSSLTSEDSAVY YCARSVWLRRDFAYWGQGTLVTVSA |
| 5 | Light chain: CDR1 | KSSQSLLNSSNQKNYLA |
| 6 | Light chain: CDR2 | FASTRES |
| 7 | Light chain: CDR3 | QQHYSTPLT |
| 8 | Heavy chain: CDR1 | GYTFSSYWIE |
| 9 | Heavy chain: CDR2 | EILPGSGSTNYNEKFKG |
| 10 | Heavy chain: CDR3 | SVWLRRDFAY |
| 11 | Human 14-3-3 epsilon isoform 1 | MDDREDLVYQAKLAEQAERYDEMVESMKKVAGMDVELTVEERNLLSV AYKNVIGARRASWRIISSIEQKEENKGGEDKLKMIREYRQMVETELK LICCDILDVLDKHLIPAANTGESKVFYYKMKGDYHRYLAEFATGNDR KEAAENSLVAYKAASDIAMTELPPTHPIRLGLALNFSVFYYEILNSP DRACRLAKAAFDDAIAELDTLSEESYKDSTLIMQLLRDNLTLWTSDM QGDGEEQNKEALQDVEDENQ |
| 12 | Human 14-3-3 epsilon isoform SV | MVESMKKVAGMDVELTVEERNLLSVAYKNVIGARRASWRIISSIEQK EENKGGEDKLKMIREYRQMVETELKLICCDILDVLDKHLIPAANTGE SKVFYYKMKGDYHRYLAEFATGNDRKEAAENSLVAYKAASDIAMTEL PPTHPIRLGLALNFSVFYYEILNSPDRACRLAKAAFDDAIAELDTLS EESYKDSTLIMQLLRDNLTLWTSDMQGDGEEQNKEALQDVEDENQ |
| 13 | Epitope 1 | FSVFYYEILNSPDRACRL |
| 14 | Epitope 2 | HPIRLGLALNFSVFYYEI |
| 15 | Epitope 3 | FSVFYYEILN |
| 16 | Heavy chain: AA sequence with leader | MEWTWVFLFLLSVTAGVHSQVQLQQSGAELMKPGASVKISCKATGYT FSSYWIEWVKQRPGHGLEWIGEILPGSGSTNYNEKFKGKATFTADTS SNTAYMQLSSLTSEDSAVYYCARSVWLRRDFAYWGQGTLVTVSA |
| 17 | Light chain: AA sequence with leader | MESQTQVLMFLLLWVSGACADIVMTQSPSSLAMSVGQKVTMSCKSSQ SLLNSSNQKNYLAWYQQKPGQSPKLLVYFASTRESGVPDRFIGSGSG TDFTLTISSVQAEDLADYFCQQHYSTPLTFGAGTKLELK |

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense.

Introduction to the Examples.

Ionizing radiation (IR) is a commonly employed treatment method for many types of human cancers. Targeted therapy can result in effective treatment of cancer without the systemic side effects of radiation or chemotherapy treatment alone, however remains one of the biggest challenges to develop. Due to tumor heterogeneity, not all cancers respond to a particular treatment regimen with similar efficacy. Thus, there is an urgent need to develop targeted therapies that are not only highly specific to cancer but also have minimal toxicity towards normal tissues surrounding tumors. IR treatment can achieve cell killing through DNA strand breaks and can illicit phenotypic changes in the cells resulting in molecules being expressed on the surface of tumor cells. These molecules are termed neo-antigens or radiation inducible proteins. In addition, a limited number of tumor associated antigens presently serve as targets for radio-immunotherapy. As such these radiation-inducible antigens can serve as potential targets for therapeutic antibodies, radio-immunotherapy, and targeted drug delivery molecules that specifically target the tumor. The elimination of cancer with antibodies is based upon recruitment of host effector mechanisms either through complement activation or Fc-receptor dependent responses.

Lung cancer is a leading cause of death worldwide. In the United States in 2014, the NCI estimated 224,210 new cases and 159,260 deaths from lung cancer of non-small cell and small cell combined. Among all lung cancer cases, NSCLC is the most common type, with about 85%-90% of all cases, and is commonly non-responsive to chemotherapy.

We set out to find out an antibody for use on irradiated tumor cells. The neo-antigen discussed herein was discovered and prioritized after radiation treatment of H23 cells by subtractive immunization. Subtractive immunization is an approach to generate monoclonal antibodies (McAb) against poorly immunogenic or rare antigens. Two steps are involved in this process. The first step involves 'tolerization' where the mice are immunized by normal sets of antigen after which the mice are immune-suppressed by cyclophosphamide. After immune-suppression, the mice are immunized a second time to generate antibodies against rare antigens. This study used irradiated human lung cancer cells to create neoantigens and then inoculated these neoantigens into the mice. Following boosts with irradiated tumor cells, B cells from spleens were harvested and hybridomas were created by fusion with myeloma cells. The hybridomas were screened with irradiated human lung cancer cells in a high throughput screening method. After the positive clones were identified, clones of antibodies were purified and evaluated by binding to irradiated tumor cells, immune response and characterization of the neo-antigen.

In this study, one antibody, 7D4, bound best to the irradiated H23 lung cancer cells in vitro through immunohistochemistry, IF, FACS and in vivo by mouse imaging. An immune response was elicited in vitro by mouse dendritic cell (MDC) with phagocytosis of irradiated H23 tumor cells in combination with 7D4 antibody treatment. The dendritic cells engulfed the tumor cells by the receptors to the Fc domain of the antibody so that the MDC could more readily bind to the antibody and opsonize the tumor. In an in vivo study, mice were injected IV with the candidate 7D4 antibody, radiated tumor cells and MDC to check for interferon gamma level (INF-γ) through isolated lymphocytes from spleen. IFN-gamma is a cytokine that is critical for adaptive and innate immune response against viruses, tumors and indicate T cell activation against the tumor cells.

The antigen bound by antibody 7D4 was characterized and identified to be approximately 27 kDa by SDS-PAGE and Western-blot after radiation treatment of the tumor cells. The antigen was proteomics sequenced and the result was shown to be a 14-3-3 epsilon protein. IHC was used to confirm the binding on the treated H23 tumor cell. The 14-3-3 epsilon protein is an adaptor protein implicated in the regulation of a large spectrum of both general and specialized signaling pathway. It binds to a large number of partners, usually by recognition of a phosphoserine or phosphothreonine motif. The binding generally results in the modulation of the activity of the binding partner. 14-3-3 epsilon coordinates the cross talk between the MAPK signal module and other molecular pathways/biological processes primarily including protein metabolism and synthesis, DNA repair, and cell cycle regulation.

Example 1

Generation of the 7D4 Monoclonal Antibody

Irradiation of cancer elicits a stress response with transport of stored proteins to the surface of cancer cells. These inducible surface proteins can be exploited as targets for antibody based immunotherapy to destroy cancer cells. In order to develop monoclonal antibodies (McAb) targeted to radiation-inducible neoantigens, subtractive immunization was employed to produce antibodies against surface proteins on irradiated lung cancer tumor model H23.

0Gy or 3Gyx3 irradiated H23; H460 and H520 cells were used as antigen for subtractive immunization. Cyclophosphamide was used as an immuno-suppressing reagent. The mice with high immune response to irradiated cancer cells were chosen for cell fusion. The hybridomas were screened using both cells by FMAT and Dot-blot assays.

Specifically, H23 lung tumor cells were cultured in 384 well plates and were either sham irradiated or irradiated as described in Table 1. There were $1 \times 10^4$ cells per well. PBS diluted mouse sera was added to the 384 microtiter plate wells. The cells and the sera were then incubated at 37° C. in a $CO_2$ incubator for 2 hours. The plates were then treated with goat anti-mouse IgG Fc conjugated to Alexa fluor 647 dye and goat anti-mouse IgM conjugated to Alexa fluor 680 dye. The cells were then incubated overnight and were read by FMAT system (Model 8100). The results of immunized mice serum against H23 tumor cells showed that positive cells increased at day 56 and were highest at day 70 compared to day 40, which was the first boost with irradiated tumor cells (Table 2).

Figure 8A:
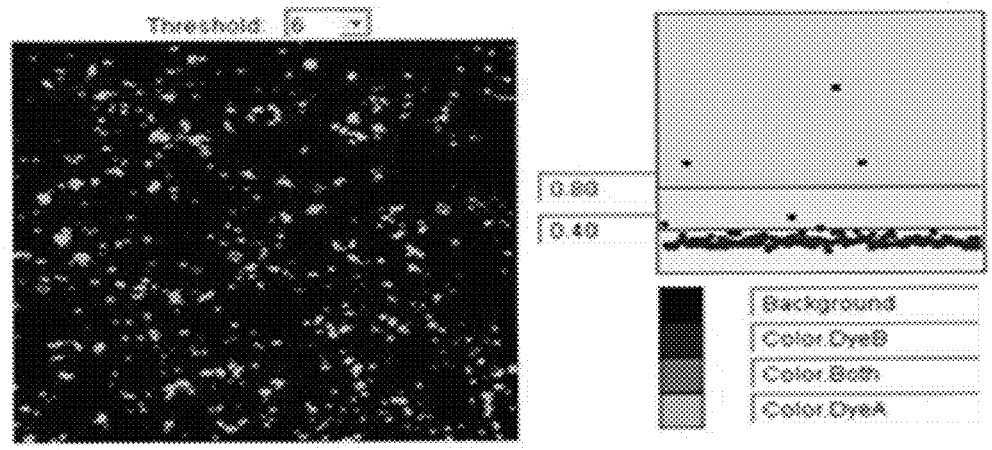
FIG. 8A depicts an image showing that clone of 7D4 showed high IgG binding on IR 3Gyx3 treated tumor cells and negative IgM binding either on 3Gyx3 or sham 0Gy treated tumor cells. Also, there is a 6 fold increase in binding on 3Gyx3 treated tumor cells relative to sham 0Gy treated cells.
Figure 8A:
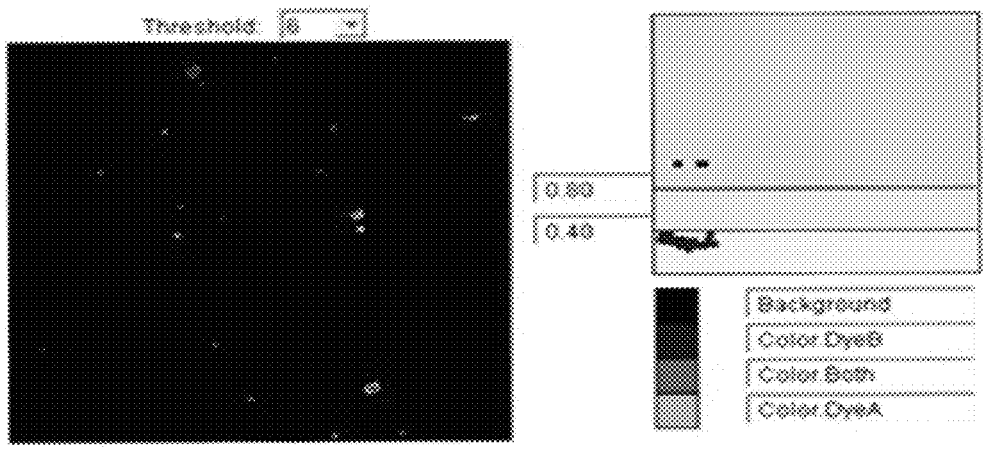
Figure 8B:
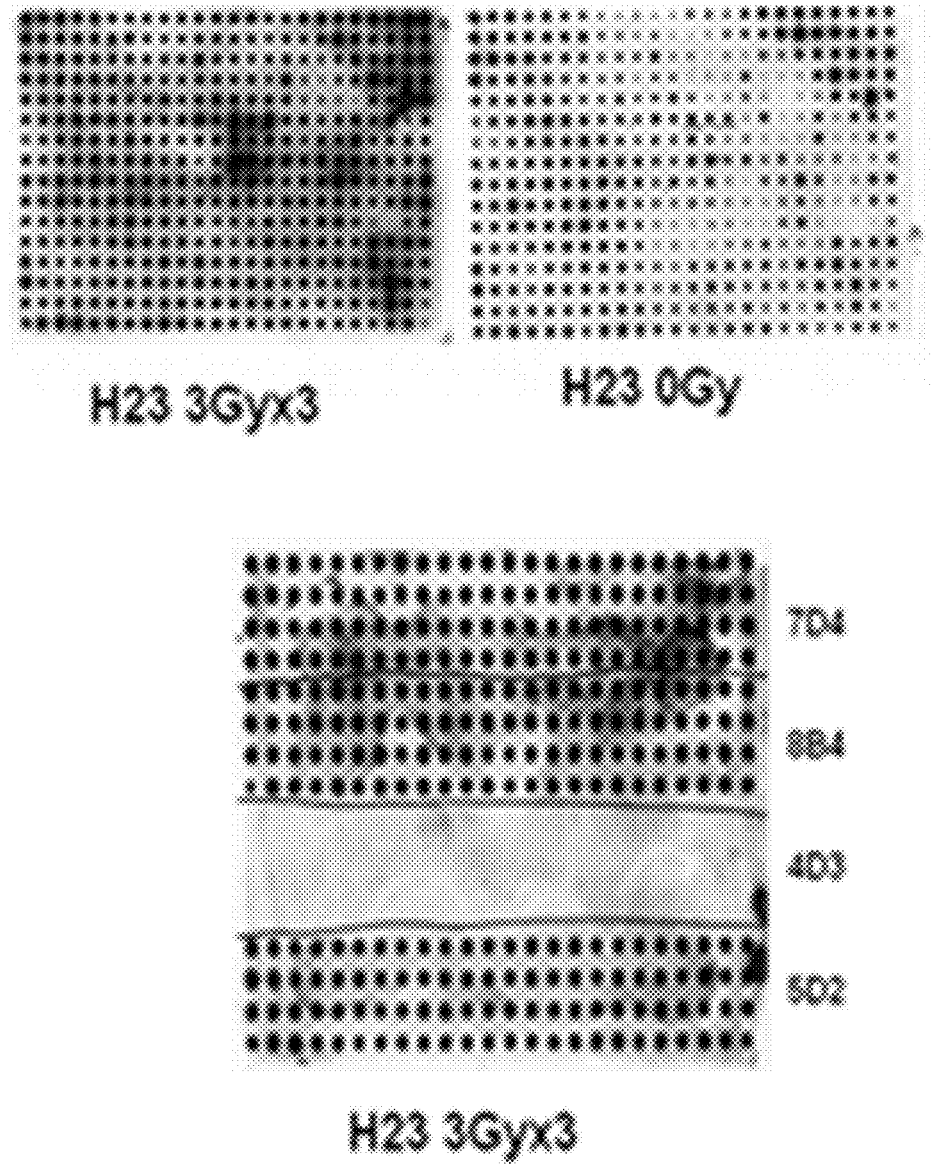
FIG. 8B depicts dot-blot images indicating that hybridoma supernatants were strongly positive on 3Gyx3 treated tumor cells and much lower on sham 0Gy treated tumor cells using the Dot-blot assay. Additionally, the bottom dot-blot shows four positive clones against 3Gyx3 treated tumor cells that were picked up from assays for hybridoma sub-cloning. Three clones, 7D4, 8B4 and 5D2, remained positive in the Dot-blot assay and 4D3 completely lost the ability to secrete antibody.

After 15 days of cell fusion, the hybridoma supernatants in culture plates were harvested and screened with FMAT and Dot-blot assays. The results indicated that hybridoma supernatants contained mouse IgG (green) and IgM (blue) (FIG. 8A). Clone 7D4 had high binding to H23 3Gyx3 treated tumor cells compared with 0Gy sham H23 tumor cells. In the 0Gy sham H23 tumor cells IgM was absent in FMAT assay. Additionally, the intensity of 3Gyx3 treated H23 cells was much higher compared with 0Gy sham H23 cells in the Dot-blot assay (FIG. 8B).

The 7D4 hybridoma clone was cultured in complete FBS medium with all supplements. The cells were harvested, counted and then frozen in hybridoma freezing medium (90% FBS+10% DMSO) in $2 \times 10^6$/vial. The cells were shipped to Genscript for antibody binding site sequence. The antibody binding site amino acid sequence in variable heavy and light chains with CDR regions are as in the following:

Heavy chain: Amino acids sequence (138 AA)
Leader sequence-FR1-CDR1-FR2-CDR2-FR3-CDR3-FR4
(SEQ ID NO: 16)
MEWTWVFLFLLSVTAGVHSQVQLQQSGAELMKPGASVKISCKATGYTF

SSYWIEWVKQRPGHGLEWIGEILPGSGSTNYNEKFKGKATFTADTSSN

TAYMQLSSLTSEDSAVYYCARSVWLRRDFAYWGQGTLVTVSA

-continued

Light chain: Amino acids sequence (133 AA)
Leader sequence-FR1-CDR1-FR2-CDR2-FR3-CDR3-FR4
(SEQ ID NO: 17)
MESQTQVLMFLLLWVSGACADIVMTQSPSSLAMSVGQKVTMSCKSSQS

LLNSSNQKNYLAWYQQKPGQSPKLLVYFASTRESGVPDRFIGSGSGTD

FTLTISSVQAEDLADYFCQQHYSTPLTFGAGTKLELK

TABLE 1

Mouse immunization schedule.
Mouse strain: BALB/C or AJ

| Cell line | H23 | H23 | H23 + H460 + H50 | H23 + H460 + H520 |
|---|---|---|---|---|
| IR treatment | 3Gy × 3 | 3Gy × 1 | 3Gy × 1 | 3Gy × 3 |
| Time interval | 0, 6, 24 h | 2 h | 2 h, cell mixture | 0, 6, 24 h, cell mixture |
| "R" | 2 × 10⁶/IP | | | |
| "RR" | | 2 × 10⁶/IP | | |
| "L" | | | 2 × 10⁶/IP | |
| "O" | | | | 2 × 10⁶/IP |

TABLE 2

| Tumor cell | IR Treatment | Days of Immunization | Positive/1000 cells |
|---|---|---|---|
| Samples of BALB/C mouse "L" | | | |
| H23 | 3 Gy/2 h | 40 | 5 |
| | | 56 | 145 |
| | | 70 | 265 |
| H23 | 3 Gy × 3/0, 6, 24 h | 40 | 10 |
| | | 56 | 200 |
| | | 70 | 235 |
| H23 | 0 Gy | 40 | 10 |
| | | 56 | 115 |
| | | 70 | 120 |
| Sample of AJ mouse "O" | | | |
| H23 | 3 Gy/2 h | 40 | 40 |
| | | 56 | 250 |
| | | 70 | 260 |
| H23 | 3 Gy × 3/0, 6, 24 h | 40 | 25 |
| | | 56 | 210 |
| | | 70 | 245 |
| H23 | 0 Gy | 40 | 50 |
| | | 56 | 125 |
| | | 70 | 135 |

Example 2

Antigen Identification and Purification

Figure 9:
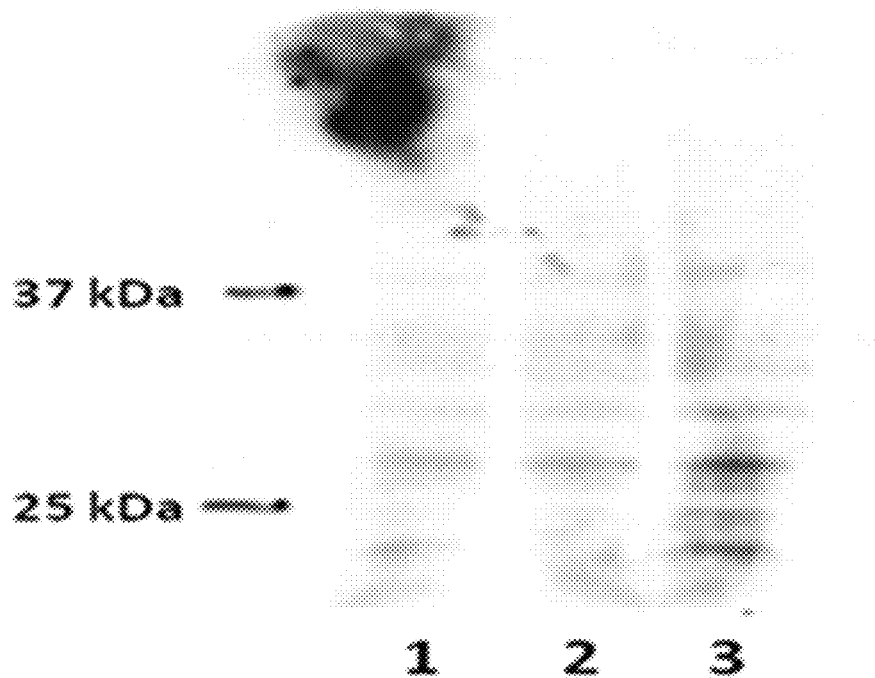
FIG. 9 depicts an immunoblot showing that McAb 7D4 reacted with H23 cell lysate. The results indicated that the staining increased in response to irradiation of H23 tumor. The protein bands were located at around 27 kDa. The intensity levels of protein bands constantly increased from sham 0Gy to 3Gyx1 with the highest level observed in 3Gyx3 treatment.

H23 cells were grown and irradiated as indicated and cell lysates were prepared as the source of antigen. The same amount of cell lysate was loaded on each lane. The protein was separated by SDS-PAGE and transferred to a NC membrane. Western-blot assay was used for analysis of the inducible protein in cell lysates. Three bands can be observed located around 27 kDa. The intensities of bands increased from 0Gy to 3Gyx1 (FIG. 9).

Figure 10:
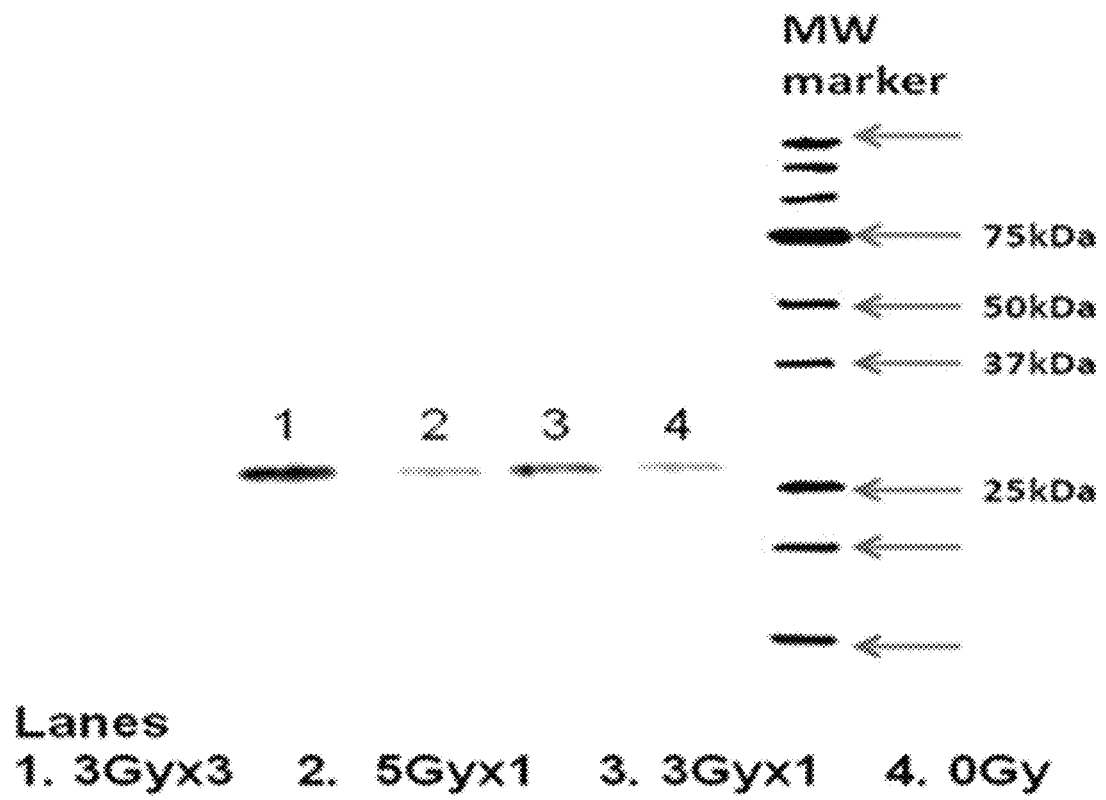
FIG. 10 depicts and immunoblot showing analysis of IP purified protein from H23 cell lysates and reacted with anti 14-3-3 epsilon antibody 7D4. The result indicated that the protein was captured by the antibody affinity beads. The molecular weight of this protein band is around 27 kDa. The protein density showing on gel was the highest in 3Gyx3 treated H23 human lung cancer cells compared to the others of 5Gyx1, 3Gy1 and sham 0Gy treated.

IR or sham 0Gy treated H23 cell lysates were prepared and specific protein was captured by a 7D4 affinity column. Eluted protein from the column was dialyzed against PBS pH 7.2 and concentrated. SDS-PAGE and Western-blot assay was then performed using the 7D4 McAb. FIG. 10 shows that the intensity of bands recognized by 7D4 McAb. The 3Gyx3 treated H23 cells had a higher intensity band compared with other treatments. The band around 27Kda was cut out and sent to Mass-Spectrometry Research Center for proteomics analysis of the protein. It was reported that the affinity purified protein band from is a 14-3-3 protein epsilon. It is composed of 255 amino acids and is coded by a GN=YWHAE, AC=P62258 OS=Homosapiens (human). The full protein sequence is as following: MDDREDLVYQ AKLAEQAERY DEMVESMKKV AGMDVELTVE ERN-LLSVAYK NVIGARRASW RIISSIEQKE ENKGGED-KLK MIREYRQMVE TELKLICCDI LDVLDKHLIP AANTGESKVF YYKMKGDYHR YLAEFATGND RKEAAENSLV AYKAASDIAM TELPPTHPIR LGLAL-NFSVF YYEILNSPDR ACRLAKAAFD DAIAELDTLS EESYKDSTLI MQLLRDNLTL WTSDMQGDGE EQNKEALQDV EDENQ (SEQ ID NO:11).

In summary, Western immunoblot showed a specific band with molecular weight of about 27 kDa using this antibody. The intensity of this band increased with the dosage of irradiation on H23 and highest intensity occurred in 3Gy×3. Proteomics analysis revealed that the 27 kDa molecule is 14-3-3 epsilon.

Example 3

14-3-3 Protein Epsilon Epitope Mapping

The human 14-3-3 epsilon epitope and human 14-3-3 epsilon isoform SV epitope recognized by antibody 7D4 was determined by epitope mapping using peptides from whole human 14-3-3 protein epsilon sequence (Sigma Aldrich). These peptides span the full length of human 14-3-3 epsilon isoform 1 and 14-3-3 epsilon isoform SV. Each peptide contains 18 amino acids from N-terminal to C-terminal. Two amino acids overlap in each peptide, for a total of 31 peptides.

Two batches of purified anti 14-3-3 epsilon monoclonal antibody 7D4 were used for testing all 31 peptides by ELISA. Three concentrations of each peptide had been used for coating ELISA plate at 30, 15, 10 µg/mL, 50 µl/each well were reacted against diluted purified antibodies at same concentration in all assay. Similar results were obtained for each peptide concentration coated on the ELISA plate.

The epitope mapping experiments showed that the monoclonal antibody reacted with high absorbance (strong binding) to a peptide comprising amino acids 177-194 (FSV-FYYEILNSPDRACRL; SEQ ID NO:13) of 14-3-3 epsilon isoform 1 (FIG. 1), and with light to medium absorbance (moderate binding) to a peptide comprising amino acids 145-162 (HPIRLGLALNFSVFYYEI; SEQ ID NO:14) of 14-3-3 epsilon SV (FIG. 2). There is 10 amino acid shared homology (FSVFYYEILN; SEQ ID NO:15) in both recognized amino acid sequences. The data also indicated that purified anti 14-3-3 epsilon 7D4 antibody is a mouse IgG1 sub-class.

Example 4

Anti-14-3-3 Epsilon Antibody Displays Specificity for Irradiated Cancer Cells H23 human lung cancer cells were irradiated with 3Gyx3. Cells were treated with 4% paraformaldehyde and rehydrated. Cells were then treated with blocking buffer followed by the addition of the 7D4 mouse monoclonal antibody to 14-3-3 epsilon or addition of a commercial rabbit anti human 14-3-3 epsilon antibody purchased from Bio-Legend Company. Cells were then washed and incubated with the secondary antibody conjugated to HRP. Cells were then stained with DAB and counterstained with Hematoxylin.

Figure 3B:
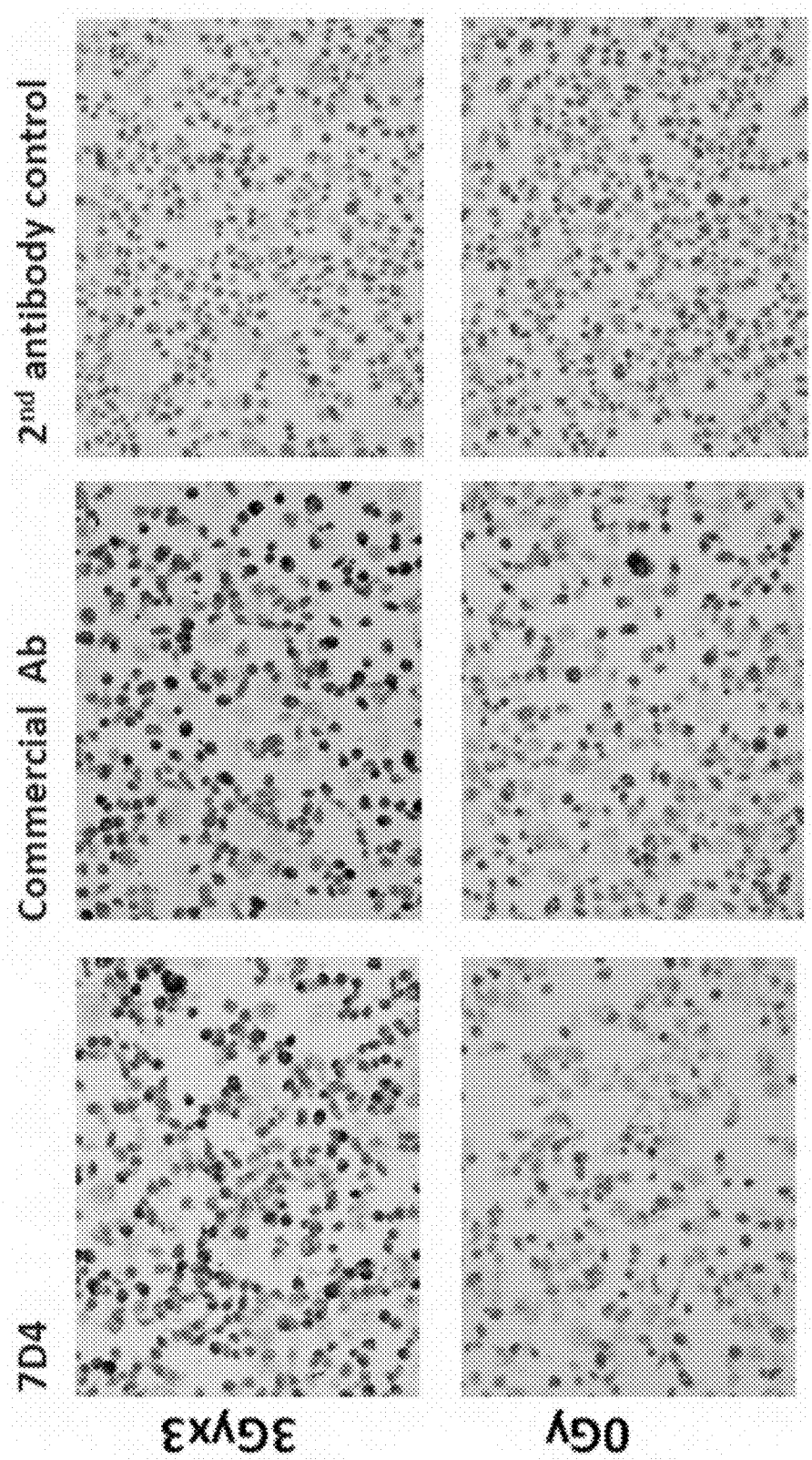
FIG. 3B shows anti-14-3-3 epsilon antibody detecting protein on H23 (NSCLC) treated with 3Gyx3 and sham 0Gy. 7D4 antibody binds to irradiated H23 cells but not non-irradiated cells. The commercial antibody shows binding to non-irradiated cells.

Shown in FIG. 3A is the immunocytochemistry of the commercial antibody binding to human lung cancer cell H23 following irradiation. Upon incubation with the commercial antibody, intensity of staining was higher in the 3Gyx3 treatment group as compared to the 3Gyx1 treatment group. However, background staining in the 0Gy treatment group was observed. Shown in FIG. 3B is the immunocytochemistry of 7D4 antibody binding to human lung cancer cell H23 following irradiation in comparison with the commercial antibody. These data show that the 7D4 mouse monoclonal antibody binds to lung cancer cells following treatment with radiation with minimal binding to cells that were not treated with radiation (lower panel). The commercial antibody to 14-3-3 was used as a positive control and shown in the center panels. This also showed that the anti-14-3-3 epsilon antibody binds following irradiation, however, there is also non-specific binding in the absence of irradiation. The negative control was secondary antibody that showed no increased binding to H23 cells without irradiation.

Figure 4A:
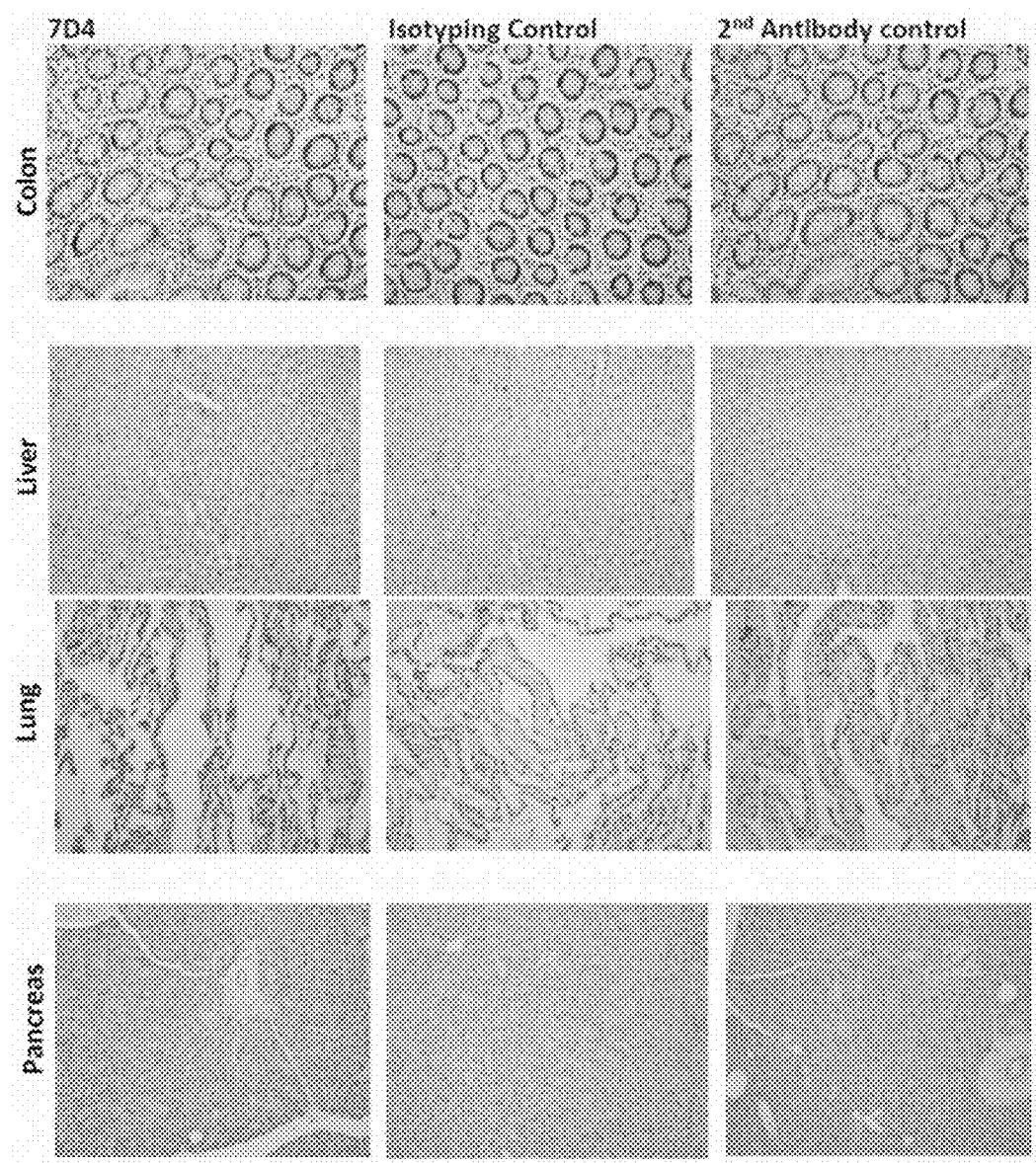
FIG. 4A and FIG. 4B show anti-14-3-3 epsilon antibody reacting with human normal tissues.
Figure 4B:
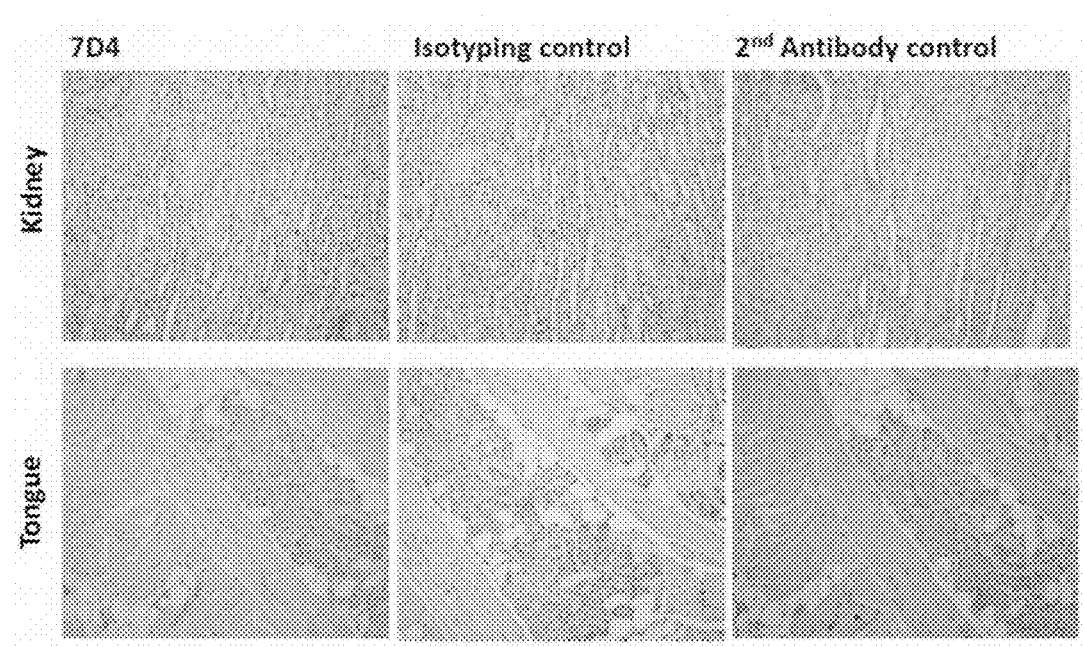

To determine normal tissue cross reactivity, antibody binding to normal tissues was evaluated. Antibody binding to colon, liver, lung, pancreas, kidney and tongue was examined (FIG. 4A, FIG. 4B). These immunohistochemistry experiments showed that the 7D4 mouse monoclonal antibody to 14-3-3 epsilon showed no binding to colon, liver, pancreas, kidney or tongue. There was minimal binding to the lung. In comparison, the isotype control on secondary antibodies showed no binding to any organ.

Figure 5:
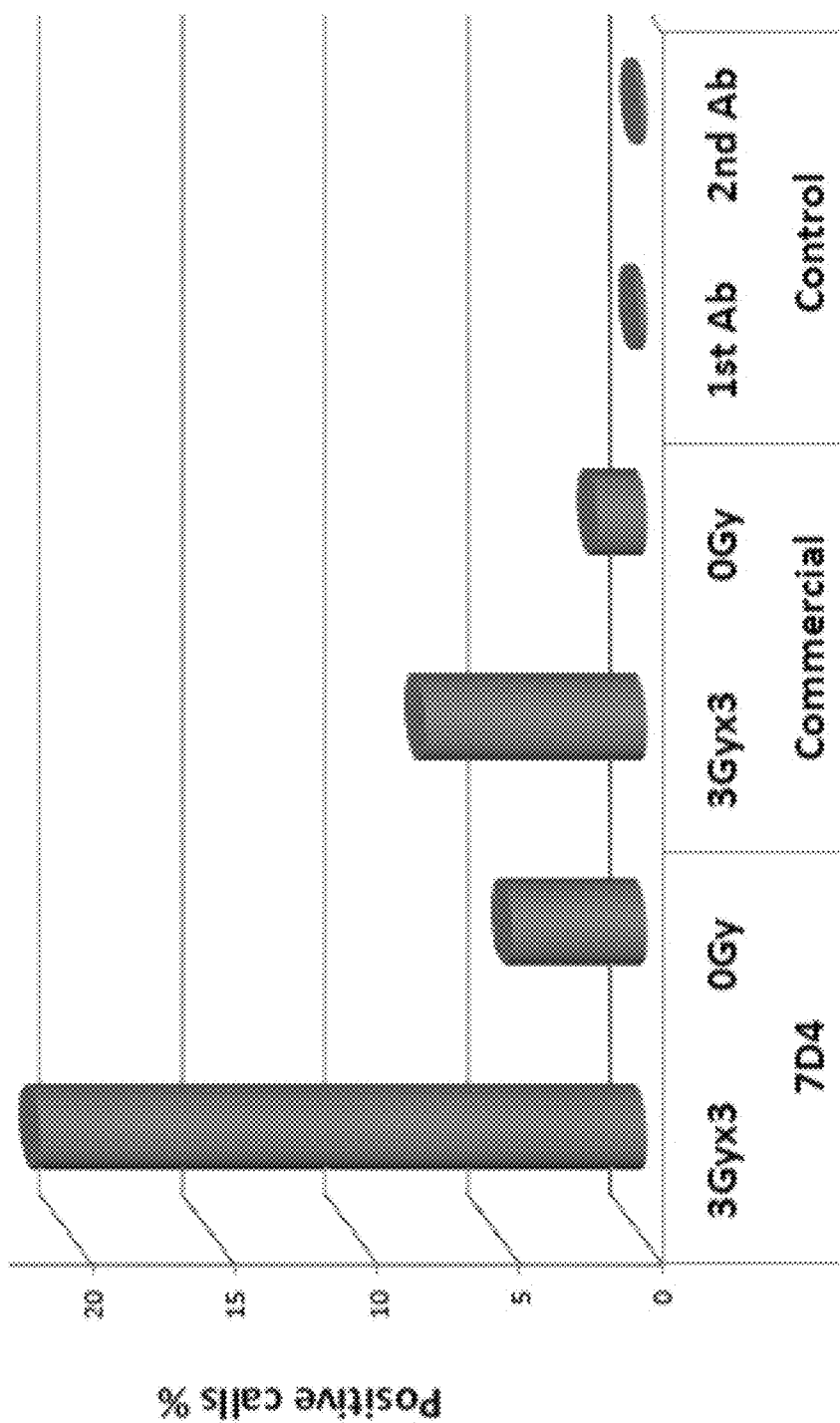
FIG. 5 shows flow cytometry of antibody binding to human lung cancer cell model H23.

H23 cells were treated with radiation, 3Gyx3 or 0Gy sham. Cells were then treated with blocking buffer followed by the addition of the 7D4 anti-14-3-3 epsilon monoclonal antibody. Cells were then washed and stained with the secondary antibody conjugated to the fluorescent marker Alexa Fluor 488. Commercial rabbit anti-human 14-3-3 epsilon antibody was used as positive control. Negative controls included 7D4 without secondary antibody and normal mouse IgG with secondary antibody. Shown in FIG. 5 is the percentage of cells staining positive with the anti-14-3-3 antibodies as measured by flow cytometry (FACS). Cells treated with 3Gyx3 showed a 20 fold increase in the percentage of cells staining positive with the 7D4 antibody following irradiation. In comparison, only 4% of cells showed positive staining with no irradiation. The commercial antibody showed less radiation induced binding as compared to the 7D4 monoclonal. Control antibodies included isotype control and secondary antibody following irradiation which showed no increase in antibody binding.

Figure 11A:
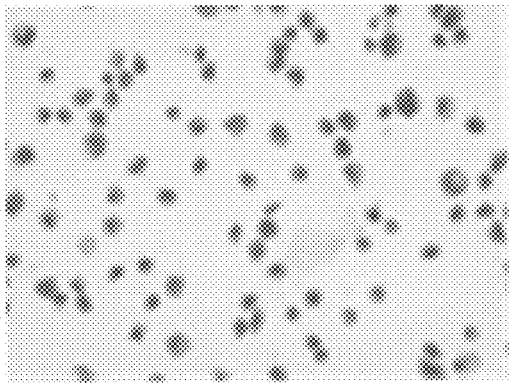
FIG. 11A depicts IHC results showing that 7D4 monoclonal antibody strongly reacts with 3Gyx3 treated H23 tumor cells and slightly or negative with sham 0Gy treated H23 tumor cells in brown color (10×40).
Figure 11A:
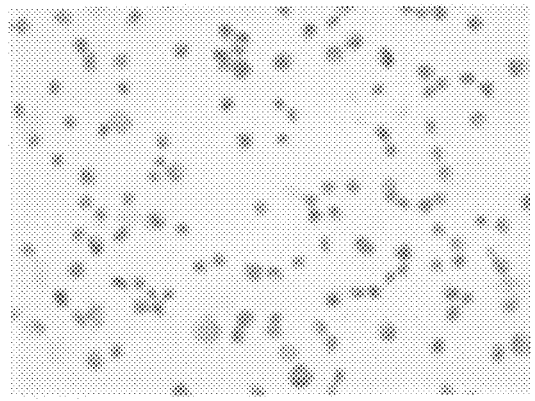
Figure 11B:
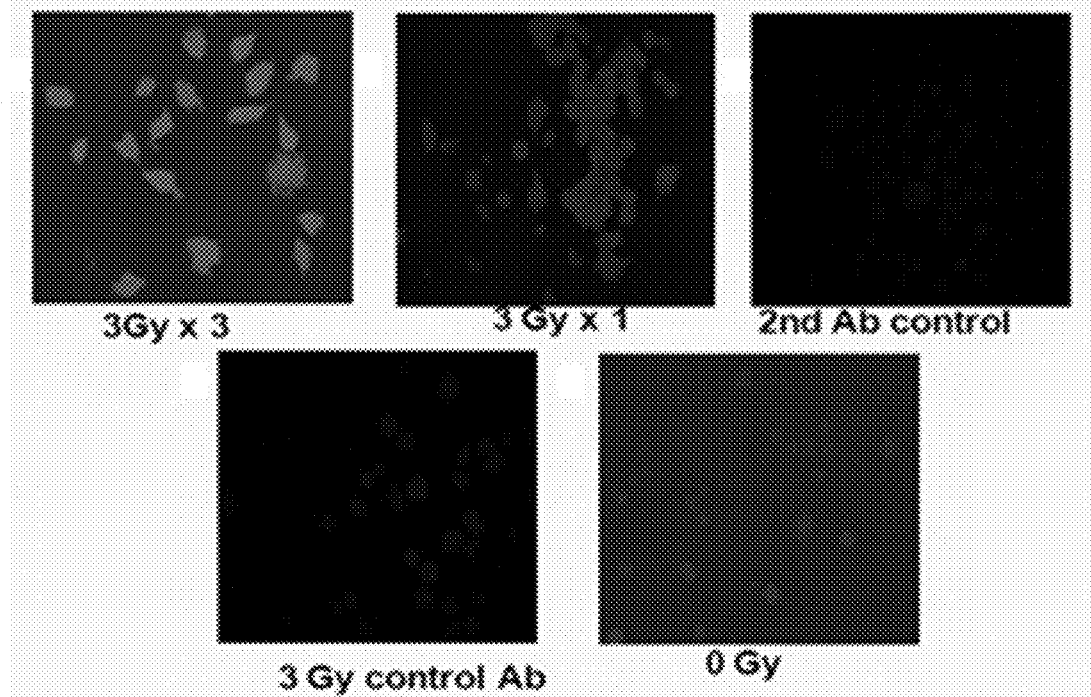
FIG. 11B depicts IF results showing similar results, high intensity staining was observed on tumor cells treated with 3Gyx3 and less intense staining was observed on 3Gyx1 treated tumor cells. Sham 0Gy cells had minimal staining. Controls of normal mouse IgG or secondary antibodies also had minimal staining on treated tumor cells (10×40).
Figure 12A:
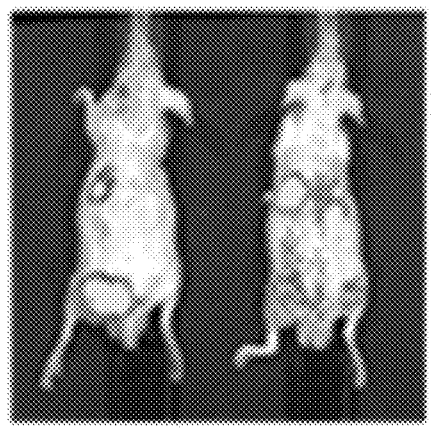
FIG. 12A, FIG. 12B, FIG. 12C and FIG. 12D depict images showing that the 7D4 mAb selectively binds to an irradiated H23 tumor in an in vivo nude mouse model for at least 10 days. H23 cells were injected into both lower extremities of nude mice. The left lower limb was irradiated with 3Gyx3 in a triplicate regimen (9Gy total). The right lower limb was shielded by lead and 0Gy sham irradiated. NIR intensity in the left hindlimbs was high and lasted 10 days. Right hind-limbs with 0Gy treated tumors were slightly positive and diminished completely at 240 hours after injection (FIG. 12A). In the 5Gy treatment group, the intensity of fluorescence was lower than the 3Gyx3 group (FIG. 12B). Sham 0Gy treated mice administered 7D4 antibody and 5Gy treated mice administered a normal mouse IgG control antibody conjugated to AF-750 were negative for fluorescence on either IR treated or sham 0Gy treated tumors at 10 days (FIG. 12C, FIG. 12D).
Figure 12A:
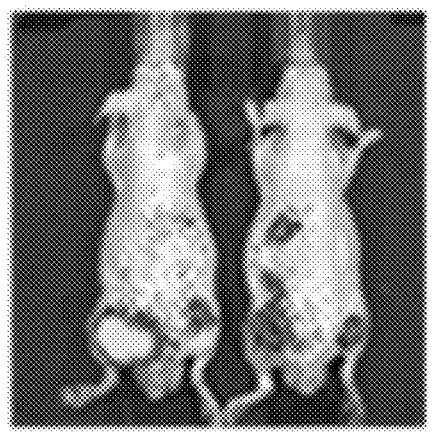
Figure 12A:
Figure 12B:
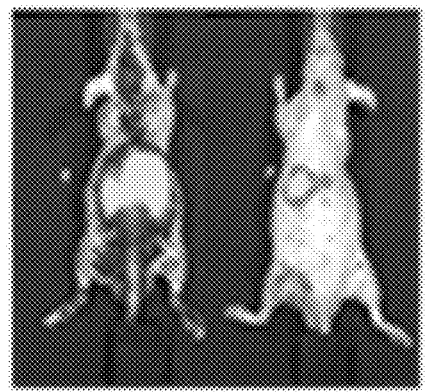
Figure 12B:
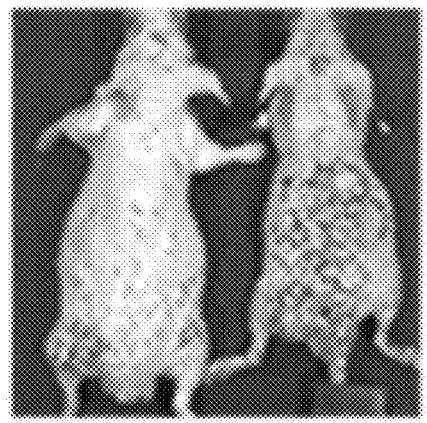
Figure 12B:
Figure 12B:
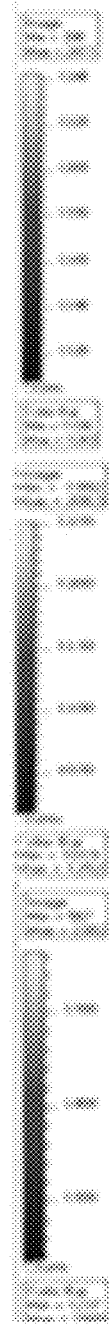
Figure 12C:
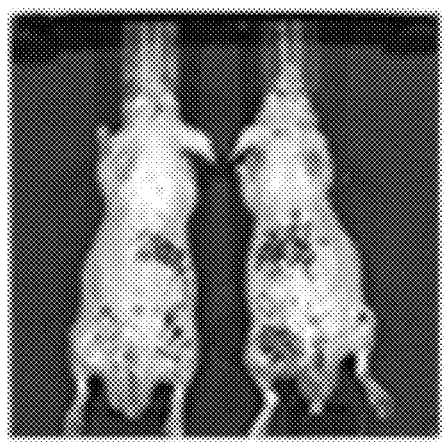
Figure 12C:
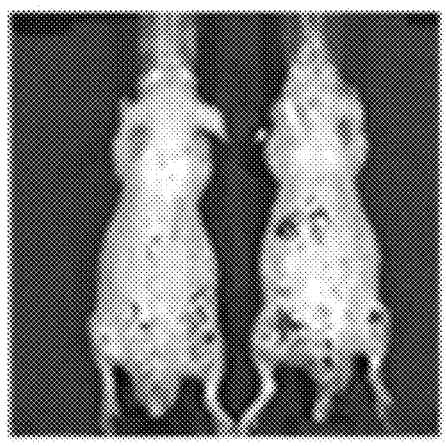
Figure 12C:
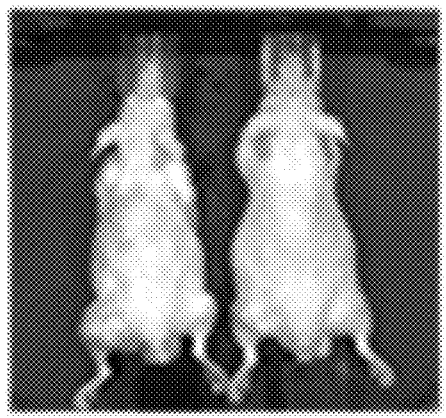
Figure 12C:
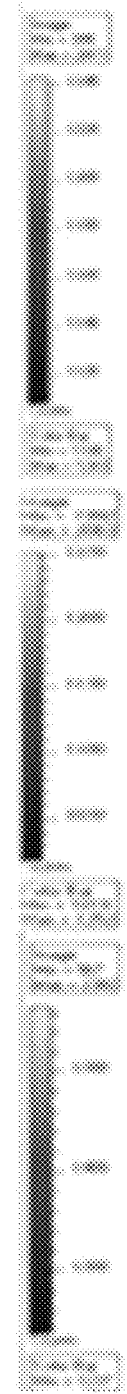
Figure 12D:
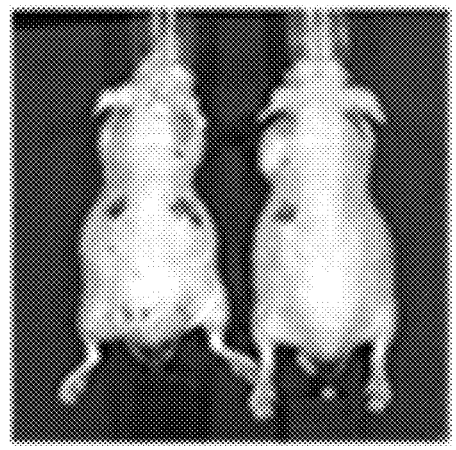
Figure 12D:
Figure 12D:
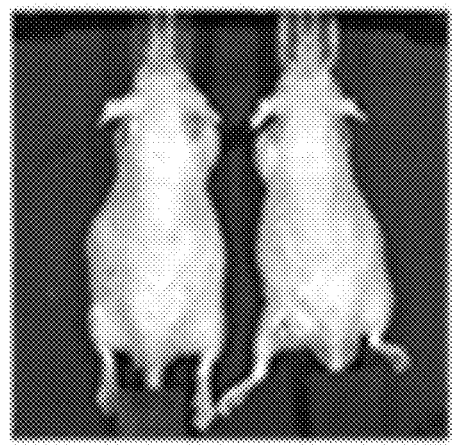

To further evaluate specificity of 7D4 for irradiated tumor cells, radiation treated tumor cells were harvested, mounted on slides, and then fixed with 4% paraformaldehyde. The slides were stained with purified 7D4 monoclonal antibody followed by a secondary goat anti-mouse IgG Fc conjugated to HRP. Substrate DAB was used for IHC or Alexa fluro 594 conjugated antibody was used for IF. IHC results indicated that purified 7D4 antibody reacted with H23 3Gyx3 irradiated cells as high intensity brown color was observed (FIG. 11A). Minimum or negative signals were observed on sham 0Gy H23 cells. The same results were observed in the IF assay as indicated by red staining in FIG. 11B. Antibody 7D4 strongly reacted with 3Gyx3 H23 cells while only minor staining on 0Gy H23 cells was observed. The controls were negative. 3Gyx1 H23 tumor cells were positive but the intensity was less than 3Gyx3 H23 tumor cells (FIG. 11B).

Taken together, these results show that monoclonal antibody 7D4 showed high specificity and affinity to irradiated H23 cells. The intensity of binding on tumor cells increased in response to irradiation while 0Gy or control antibody on irradiated H23 was negative on IHC and IF assays.

Example 5

Figure 6A:
FIG. 6A, FIG. 6B, FIG. 6C and FIG. 6D show that the 7D4 antibody activates phagocytosis by dendritic cells and monocytic cells. Murine dendritic cells (mDCs) are attracted by 3Gyx3 irradiated H23 cells coated with McAb.
Figure 6B:
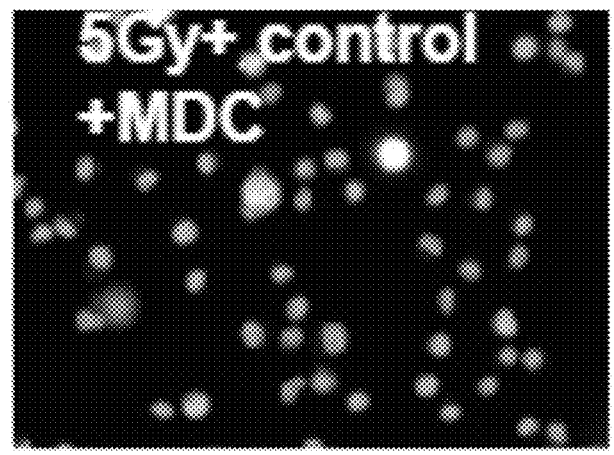
Figure 6C:
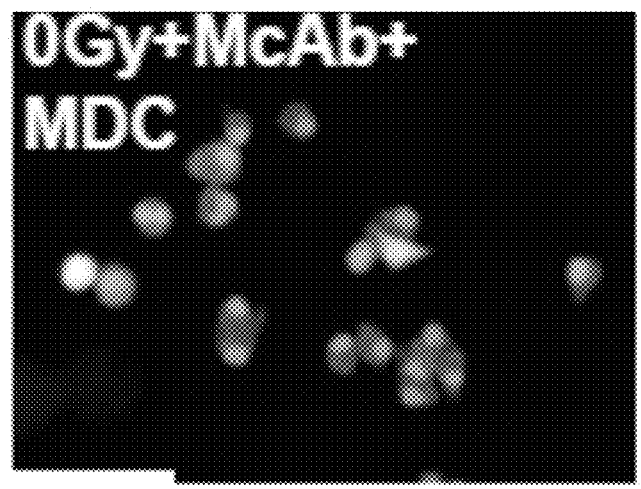
Figure 6D:
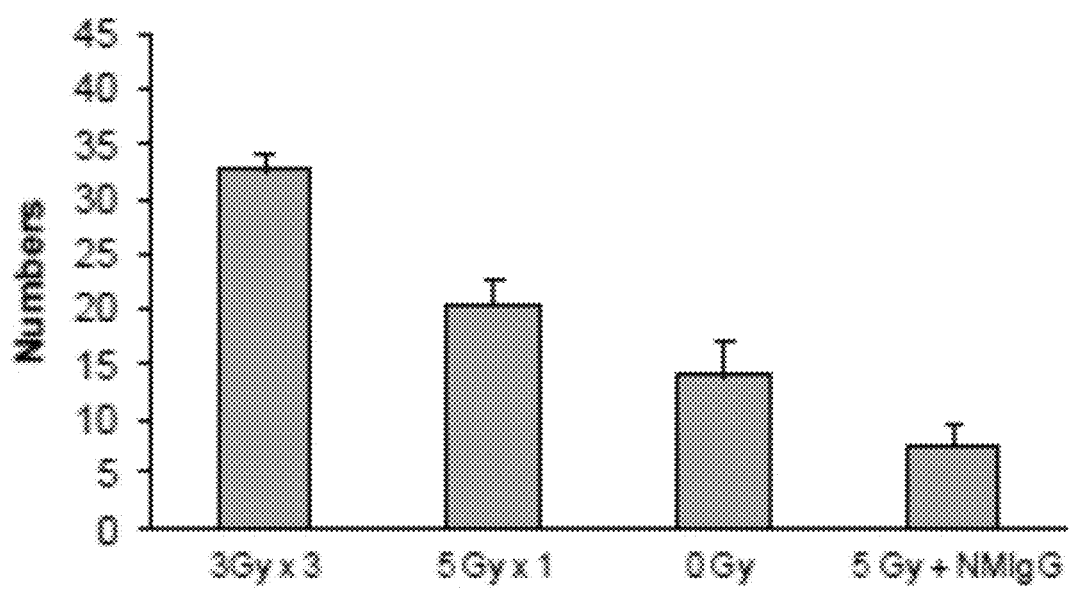

Anti-14-3-3 Epsilon Antibody Activates Phagocytosis by Dendritic Cells and Monocytic Cells Mouse dendritic cells and H23 lung cancer cells were co-cultured in vitro and measured qualitatively and quantitatively for an immune response. Phagocytosis was measured following 7D4 antibody incubation with irradiation treated H23 tumor cells. FIG. 6A shows that the 7D4 antibody activates phagocytosis by dendritic cells and monocytic cells (red staining). Extended pseudopodia and adhesions were observed in the 3Gyx3 treated H23 tumor cell. H23 cells were treated with 3Gyx3 and incubated with the 7D4 monoclonal antibody to 14-3-3 epsilon. Incubation with the antibody following irradiation activates phagocytosis of the antibody coated cancer cells. In comparison, the isotype control shows no increase in phagocytosis (FIG. 6B) nor does the absence of irradiated cells (FIG. 6C). The number of dendritic cells that activate phagocytosis were then quantified by use of flow cytometry. FIG. 6D shows the quantification of phagocytosis. H23 cells were labeled with the fluorescent marker DiI. DiI is contained in the cell membrane and is incorporated into phagocytic cells. The number of dendritic cells that engulf DiI from H23 cells was then quantified. FIG. 6D shows that H23 cells treated with 3Gyx3 activated phagocytosis in 32 cells. In comparison, lower dose irradiation activated phagocytosis in 18 cells. Cells treated with no radiation activated phagocytosis in 14 cells. The negative control was the isotype control IgG which activated phagocytosis in 7 dendritic cells.

Figure 7A:
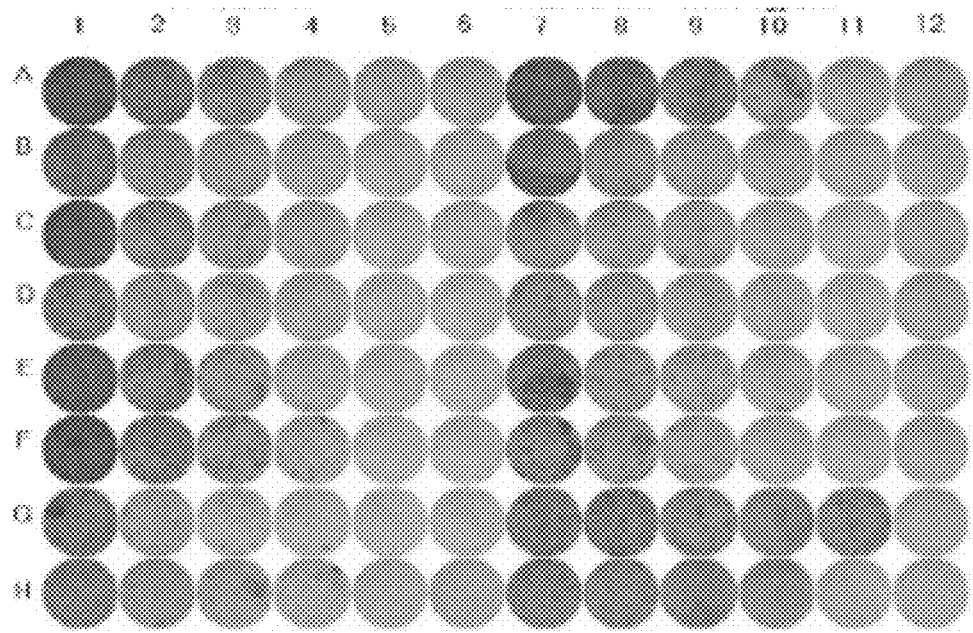
FIG. 7A and FIG. 7B show the ELISPOT IFN-γ level test in H23 cells.
Figure 7B:
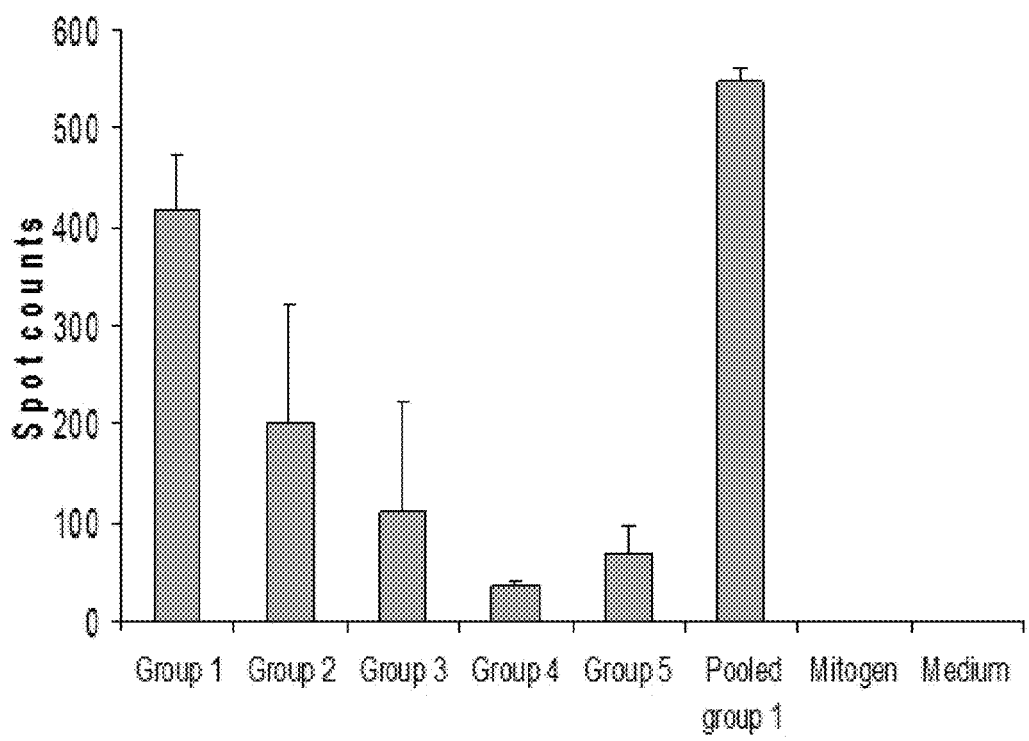

Next, irradiated H23 tumor cells were co-cultured 1:1 with activated mDCs and injected into C57 mice. Two booster injections were performed at one month intervals, and then spleens were removed. The spleens were homogenized and lymphocytes were isolated by gradient centrifugation and assayed using an anti-mouse IFN-γ antibody. Spot counts were tallied via the ImmunoSpot scanner (Cellular Technology, Ltd.). The ELISPOT shows that lymphocytes from mice injected with irradiated H23 tumor cells cultured with mouse DCs and 7D4 monoclonal antibody to 14-3-3 showed the greatest amount of IFN-γ production (FIG. 7A). FIG. 7B shows the quantification of interferon production. The number of cells producing interferon-gamma were counted. Cells treated with 3Gyx3 followed by the 7D4 mouse monoclonal to 14-3-3 and the mouse dendritic cells showed the greatest number of T cell activation (Group 1). In comparison, cells treated with radiation and antibody alone without dendritic cells showed a modest T cell activation (Group 2). Likewise, cells treated with radiation and isotype control antibody showed modest T cell activation (Group 3). Negative controls showed minimal T cell activation (Group 4 and Group 5). These findings indicate that the 7D4 anti-14-3-3 epsilon antibody can activate phagocytosis and human lung cancer antigen presentation to T cells.

In summary, ADCP and ELISPOT indicated that the antibody binds to irradiated H23 cells co-cultured with activated MDC, the phagocytic events increased with increasing irradiation dosage while 0Gy or control antibody was absent. Moreover, the IFN-γ levels on ELISPOT increased with the irradiation dosages and highest level at 3Gyx3 group. This indicated that immune responses can be triggered by the antibody through ADCP and increasing of IFN-gamma from lymphocytes.

Example 6

Antibody Binds to H23 Human Tumor in Mouse Model Imaging Assays

50 μg of AF750 fluorescent dye conjugated 7D4 antibody or 50 μg of control normal mouse IgG conjugated in 100 μl PBS were injected intravenously into irradiated or sham 0Gy tumor bearing mice. Images were recorded every 24 hours in a Kodak Imager. The NIR imaging showed that antibody signals were obtained at time points of 24, 48 and 96 hours and lasted for 10 days in 3Gyx3 treated (left hind limbs) H23 bearing mice. Control sham 0Gy treated side (right hind limbs) had much less binding signals compared with left side (in group A). The peak time was 96 hours after antibody injection in 3Gyx3 treated H23. The signal in 5Gyx1 tumor bearing mice can be seen at the same time points but the intensities were less than 3Gyx3 treated mice in both hind limbs (in group B). Controls with 0Gy sham treated plus 7D4 antibody or 5Gyx1 with controls normal mouse IgG indicated minor or no binding (FIG. 12).

In summary, near infrared images of mice showed that the fluorophore-conjugated antibody bound to irradiated tumors in the 3Gyx3 group for 240 hours while the 3Gyx1 group showed a lower level of binding. In contrast the 0Gy group and control antibody group showed minimal to no tumor binding.

Discussion for the Examples.

Ionizing irradiation (IR) is employed to treat many types of human cancers in addition to surgery and chemotherapy. Due to DNA damage during treatment, the phenotype of the cells changes, resulting in translocation of protein to the surface of tumor cells. These molecules are called IR inducible molecules or neo-antigens and are expressed in small amounts that are difficult to isolate and purify for antibody production.

In this study it was shown that subtractive immunization after radiation of the human lung cancer cells resulted in the creation of multiple antibodies to these neo-antigens. In total, 96 original positive clones and 54 sub-cloned hybridomas were picked up by FMAT and Dot-Blot assays. One of the antibodies, 7D4, showed the best binding and immune response using irradiation treated H23 cells. The 7D4 antibody showed binding to H23 in vitro and in vivo by IHC, IF and mouse NIR imaging. An immune response was generated and qualitatively shown in a phagocytosis experiment and quantitatively measured for immune response in ELIPSOT for IFN-gamma levels. The antigen was characterized by Western-blot with the 7D4 antibody at which point the antigen was sequenced to show that it was 14-3-3 epsilon. The purified antigen was reconfirmed by IHC when the 7D4 antibody bound to the irradiated H23 cell.

The antigen characterized in the H23 irradiated cell line with the 7D4 antibody treatment was 14-3-3 epsilon. 14-3-3 is a family of highly homologous proteins encoded by separate genes. There are seven protein known mammalian 14-3-3 isoforms, named with Greek letters β, ε, γ, η, δ, τζ. The MW ranged 26-29 KDa. The 14-3-3 family of proteins plays a key regulatory role in wide range of vital regulatory processes including signal transduction, checkpoint control, apoptosis, cell cycle progressing, DNA replication and nutrient-sensing pathways. 14-3-3 proteins are highly conserved and ubiquitously expressed. It has been shown to interact with CDC25 phosphatases, RAF1 and IRS1 proteins, suggesting its role in diverse biochemical activities related to signal transduction, such as cell division and regulation of insulin sensitivity[13-14]. As such, future studies will to look at tumor shrinkage models after antibody treatment, the function of this antigen and its role after radiation treatment, and the use of the 7D4 antibody for drug delivery.

Methods for the Examples.

Animals, cell lines and reagents: Animals: Four to five week old female BALB/C or AJ and C57BL/6 mice were purchased from Harlan Laboratories Inc. and maintained in Animal Facility of Office of Animal Care Welfare Assurance in School of Medicine in Vanderbilt University. All animal studies were performed in accordance with the guidelines of the IACUC and with protocols approved by Institutional Animal Care and Use Committee in Vanderbilt University.

Cell Lines: Three human lung cancer cells (H23, adenocarcinoma, non-small cell lung cancer; H460, carcinoma, large cell lung cancer; and H520, squamous cell carcinoma) were purchased from ATCC (American Type Culture Collection, Manassas City, Va., USA). The tumor cells were maintained in RPMI 1640 medium with the supplements of 2 mM L-glutamine, penicillin plus streptomycin, 10% fetal bovine serum, after which it was split every three days. SP2/O myeloma cells were kindly provided by Dr. Clint E. Carter in the Department of Biological Sciences at Vanderbilt University, Nashville, USA.

Chemicals: HAT (hypoxanthine, Thymidine and Azaserine); Cyclophosphamide; DAB subtract PHA-L and PMA mitogens; Proteinase inhibitor cocktail (Sigma); Fetal Bovine serum was pre-selected for cell fusion and purchased from Gemini Bio-Products, CA; PEG 1500 (Roche, cat. #10817300); DiI dye (Biotium Inc).

Reagents: Murine Granulocyte macrophage-colony stimulating factor (GM-CSF, ProSpec, Israel) Recombinant murine tumor necrosis factor α (TNFα) (Pierce, Ill.); Recombinant mouse CD40 Ligand/TRAP (Biovision Research Products, Mountain View, Calif.); Lympholyte-M (Cedarlane Laboratories LTD. Ontario, Canada); IFN-γ detection kit (BD Biosciences, San Diego, Calif.); Goat anti mouse IgG Fc γ specific—HRP (Jackson Immuno Research); Goat anti mouse IgG Fc-Alexa fluor 647 conjugate (Molecular Probes); Goat anti mouse IgM—Alexa Fluor 680 conjugate (Molecular Probes); Rabbit anti 14-3-3 epsilon antibody (BioLegend Company); M-pre Mammalian protein extraction reagent (Pierce, Ill.); Alexa Fluor 750 (Molecular Probes).

Subtractive Immunization: Antigens: Human Lung Cancer cell lines: (A) NCI—H23, Non small cell lung cancer, adenocarcinoma; (B) NCI—H460, Large cell lung cancer, carcinoma; and (C) NCI—H520, Squamous cell carcinoma.

Treatment of lung cancer cells with irradiation for subtractive immunization: The cultured tumor cells in Petri-dishes were exposed to X-ray (80kVp x-ray generator (Pantak North Branford, Conn., USA) with doses of 3Gyx1 or 3Gyx3 with 6 hours intervals or sham 0Gy when the cells became 75% confluent. The irradiation schema is shown in Table 1. After treatment, culture medium in the dishes was removed, the cells were washed three times with warmed PBS and then detached with pre-chilled 4° C. PBS. Three kinds of untreated tumor cells were used for primary injection and treated tumor cells were used for the secondary and boost immunization of the mice in the following four groups: (1) H23: 3Gyx3 irradiated at 0, 6, 24 hours over 24 hour period; (2) H23: 3Gyx1 irradiated cells and incubated 2 hours after treatment; (3) H23+H460+H520: 3Gyx1 irradiated individually, incubated for 2 hour after treatment and then mixed together for immunization; and (4) H23+H460+H520: 3Gyx3 irradiated individually at 0, 6, 24 hours and then mixed together for immunization.

Mice Immunization Schedule: Balb/C and AJ mice were pre-bled, sera separated and stored in −80° C. for self negative controls. The immunization was as following: On day 0, $2 \times 10^6$ non-irradiated human lung cancer cells were intraperitoneal (IP) injected. On day two and day four, cyclophosphamide was IP injected at 200 mg/kg to suppress antibody production to non-irradiated lung cancer cells. On day 18, irradiated human lung cancer cells were injected for subtractive immunization (See Table 1). On day 40 and 56, the mice were boosted with irradiated human lung cancer cells. On day 70, the mice were hyper-immunized with irradiated cancer cells. All the mice were bled on day 0, 18, 40, 56 and day 70 and the sera were collected for antibody titer screening by a Dot-blot and FMAT analysis. Three days prior to cell fusion, the high antibody titer B cell donor candidate mouse was boosted with irradiated tumor cells again. Four mice/group/strain of mouse were used in the immunization. At day 0, all mice were injected with non-irradiated tumor cells. At day 2 and day 4, the mice were injected cyclophosphamide and then mice primary or boost immunization with IR tumor cells at days 18, 40, 56 and 70, cell numbers were as above.

Immunized mice sera screening: Dot—Blot Assay: Treatments of human lung tumor cells were described in Table 1. IR or sham treated tumor cells were collected and resuspended in PBS. The cells were coated on a nitrocellulose membrane with $4 \times 10^6$ cells per $7.5 \times 11.5$ cm$^2$ membrane. The membranes were air dried, washed three times with PBS containing 0.1% Tween 20, and air dried again. The pre-diluted immunized mice sera starting from 1/1000 and then 1:2 dilution until 1/64,000 stored in 384 well plates was replicated onto the appropriate membrane by a replicator with 384 pins and then incubated for 2 hours at room temperature (RT) in a humid chamber. After washing three times with the same buffer as above, membranes were blocked with 5% non-fat dry milk (NFDM)+0.5% BSA in the buffer for at least 45 minutes and washed again. The membranes were incubated with 1:4,000 diluted goat anti mouse IgG Fc gamma chain specific antibody that was conjugated to the HRP enzyme for two hours. The membranes were then washed 3×5 minutes; ECL was applied for 2 minutes. The films were developed to pick up the positive screen where it was viewed on dot blot films on a light box.

FMAT-HTS (Fluorometric Microvolume Assay Technology, High Throughput Screen System): The lung tumor cells were cultured in 384 well plates with $1 \times 10^4$ cells per well and were either sham irradiated or radiated at the same dosage as described in Table 1. The diluted sera were added to the designated wells and then incubated at 37° C. in a $CO_2$ incubator for 2 hours. The cells were then reacted with goat anti-mouse IgG Fc conjugated to the Alexa fluor 647 dye or goat anti-mouse IgM conjugated to the Alexa fluor 680 dye and incubated overnight. The plates were read by FMAT machine (Applied Biosystems, Model 8100) the next day for mouse IgG and IgM levels in immunized mice sera.

Cell fusion and hybridoma screening: Cell Fusion: Mice chosen from BALB/C and AJ immunized groups with higr titres of antibody were sacrificed and the spleen was removed aseptically and stored in separate dishes with plain RPMI 1640 medium. The spleen was dissociated into single cells by a homogenizer and collected into a 50 ml sterile centrifuge tube. The spleen cells were washed three times with pre-warmed plain RPMI 1640 medium for cell fusion. Pre-cultured Sp2/O myeloma cells were collected in a sterile 50 ml centrifuge tube and washed three times with pre-warmed plain RPMI 1640 medium also. After centrifugation of spleen and the Sp2/O separately, the medium was removed and cells were re-suspended in 5 ml of the same medium individually. The cells were counted and combined at a ratio of spleen cell: Sp2/O cell of 2:1 or 5:1, then centrifuged. The supernatant was removed, and mixed cells were washed once again and then the medium was removed completely, the pellet was gently resuspended and loosened by finger flicking. 1 ml of PEG1500 was added slowly to perform cell fusion within 1 to 3 minutes. Afterwards, plain RPMI 1640 medium was added to stop the reaction. The cell suspension was incubated at 37° C. for 5 minutes, and then centrifuged at low speed, the supernatant was removed. The cell pellet was gently re-suspended in a HAT medium and dropped into the culture plates. The culture plates were transferred in a 37° C. $CO_2$ incubator to select culture the hybridomas. After 7 days of culture, HAT medium was removed, fresh HAT medium was replaced and grown for another 7-10 days in a $CO_2$ incubator for hybridoma screening.

Hybridoma screen: Fifteen days after the cell fusion, antibodies in the supernatant were tested by FMAT and Dot-Blot. The positive clones were plated into 24 well plates with the HAT medium so that the hybridoma could grow and then replaced with complete FBS medium; the supernatants were collected and assayed once again by FMAT and Dot-Blot to confirm, then positive clones were ready for sub-cloning.

Hybridoma sub-cloning, positive clone freeze, antibody production and purification: Positive hybridomas were sub-cloned into 384 well plates using limited dilution. The supernatants were tested again by Dot-Blot and FMAT. Sub-cloned positive clones were transferred into 24 well plates for freezing and expanding culture in serum free (SF) medium. Antibody was purified from accumulated SF supernatants with Protein G and Protein A columns. The purified IgG was dialyzed against 4 liter PBS at 4° C. with two changes. The concentration was tested by spectrophotomatry and IgG sub-class was distinguished using an isotyping kit (Southern Biotech, Birmingham Ala.).

IHC (Immunohistochemistry) or IF (Immunofluorescent) stain: The H23 cells were cultured in RPMI 1640 medium supplemented with 10% FBS plus Penicillin, streptomycin in $10 \times 10$ cm$^2$ Petri dish. The cells were irradiated with either 3 Gy/2h, 3 Gyx3/0, 6, 24 hrs or sham 0Gy treatment when 75% confluent. The culture medium was discarded; the tumor cells were rinsed by warmed PBS three times, and then detached with pre-chilled PBS. The cells were counted and centrifuged at 1,200 rpm for 5 minute and the supernatant was discarded. The cells were resuspended in fresh PBS and $1 \times 10^5$ cells were mounted on pre-clean Fisher Brand Superfrost microscope slides. The cells were air dried, fixed with 4% buffered paraformaldehyde for 10 minutes, and then air dried again, and stored at −20° C. Immunohistochemistry (IHC) or immunofluorescence (IF) was performed by using the purified monoclonal antibodies. The slides were re-hydrated and washed three times with PBS, and then endogenous hydrogen peroxidase (HRP) was blocked (if a hydrogen peroxidase conjugated secondary antibody was used). The slides were blocked with 5% BSA+5% normal goat serum in PBS for 30-45 minutes. After blocking, the diluted purified monoclonal antibodies were added onto the slides, and then incubated for 2 hours in a humid chamber at room temperature. After washing 3× with PBS, a secondary goat anti mouse IgG Fc conjugated to HRP or conjugated to Alexa Fluor 594 was added onto the smears, then incubated for 1.5 hour at room temperature. The slides were washed three times with PBS then DAB was applied onto the cell smears for 2-5 minutes (HRP 2nd Ab). The reaction was stopped by rinsing with d-water at which point it was counterstained with Hemotoxyline. The slides were de-hydrated and mounted with cover slips.

Flow cytomery assay (FACS): H23 lung cancer cells were cultured and irradiated as above. $1 \times 10^5$ cells were incubated with primary purified McAb and then washed three times with PBS by centrifugation. A goat anti mouse IgG Fc γ chain specific secondary antibody conjugated with FITC was added to an individual tube and incubated for one hour. The samples were washed three times then analyzed by Flow cytomety assay (MACS Quant Analyzed, Miltenyl Biotec).

Dendritic cell phagocytosis through Fc receptors in vitro assay (ADCP): Preparing Mouse Dendritic Cells: Immature mouse dendritic cell (MDC) line JAWSII was obtained from American Type Culture Collection (ATCC, Manassas Va., USA.) The immature mouse dendritic cells were grown in a 100×20 mm dish with RPMI 1640 medium with 10% IgG depleted fetal bovine serum plus antibiotics and 5 ng/ml of GM-CSF. Once the MDCs were 50-60% confluent, the MDCs were harvested by detaching with 0.05% trypsin-EDTA. The cells were washed with medium, then resuspended in medium and dispensed into a small culture dish (35×10 mm) with sterile 22×22 mm cover slips. The MDCs were grown overnight in a 37° C. $CO_2$ incubator. After overnight incubation, the JAWSII cells were activated and matured in vitro with 20 ng/ml of TNF-α and 200 ng/ml of CD40 ligand/TRAP. The dendritic cells were cultured in a $CO_2$ incubator for 48 hours until confluent.

Preparing the H23 human lung tumor cells: The H23 cells were cultured in IgG depleted FBS medium until the cells became confluent at 70%. The H23 cells were irradiated with X-ray treatments or sham 0Gy radiated as above. The culture medium was removed and rinsed with warmed PBS three times. The cells were detached with cold PBS and counted. The tumor cells were incubated with purified monoclonal antibody in PBS in 10 μg/ml for 1-2 hours and washed with warmed PBS three times. The cells were spun down at 1000 RPM for 5 minutes, then resuspended in fresh PBS and stained with DiI dye at 2 μg/ml in PBS for 30 minutes in the 37° C. $CO_2$ incubator. Finally, the cells were washed with warmed PBS 3 times to remove free dye.

Co-culture of mouse dendritic with H23 rumor cells for Phagocytosis: The antibody reacted and DiI stained H23 cells were added to the matured MDC dishes in a 1:1 ratio. These cells were co-cultured overnight in the $CO_2$ incubator at 37° C. The next day, the cultured medium was removed and the cells were rinsed 3 times with warmed PBS. The cells were fixed with 10% formalin for 8 minutes. The cells were then washed with PBS 3 times again and stained with DAPI at 10 μg/ml for 10 minutes followed by washing with PBS 3 times. The slides were mounted on coverslip with 80% glycerol for ADCP events viewing.

ELISPOT assay: C57BL6/J Mice Immunization: The H23 and MDC mixture was prepared as above. Antibody coated either IR or sham 0Gy treated H23 tumor cells and controls were included in this assay. $2 \times 10^6$ cells in 0.1 ml PBS were injected into C57BL/6 mice by intraperitoneal (IP) injection. There were 3 mice/group for primary immunization. The mice were boosted twice after the first immunization by the same treatment and cell number, with the last boost being performed three days prior to termination. Three days after the boost, the mouse spleen was harvested aseptically into individual tubes containing RPMI 1640 medium for lymphocyte isolation.

Prepare Lymphocyte suspension:

The spleen was homogenized into single cells in plain RPMI 1640 medium and the cell concentration was adjusted to a maximum of $1.0 \times 10^7$ nucleated cells/ml. 5 ml of the cell suspension was added to a 15 ml centrifuge tube where a large Pasteur pipette was put at the bottom of the tube. Lympholyte-M was slowly added to the Pasteur pipette and layered under the cell suspension. The suspension was centrifuged at 1,000-1,500 g for 20 minutes at room temperature. After centrifugation, the lymphocyte layer at the interface which was harvested carefully and transferred to a new centrifuge tube. The cells were washed 3 times with plain RPMI 1640 medium at 800 g for 10 minute to pellet the lymphocytes. The lymphocytes were re-suspended in plain RPMI 1640 and counted, then diluted in plain RPMI 1640 to a designed concentration for use in the next step.

ELISPOT to measure of INF-γ level: ELISPOT was employed for measuring of IFN-γ levels generated in immunized C57BL/6 mice in vivo. The IFN-γ detection kit was used for the test and the protocol was followed as per the company datasheet. Briefly, the ELISPOT plate was coated with 100 μl of diluted IFN-γ capture antibody in the concentration of 5 μg/ml in PBS and incubated at 4° C. overnight. The plate was washed with blocking buffer and blocked with 200 μl of this buffer for 2 hours. The lymphocytes were added to designed wells in the amount of $1.0 \times 10^6$, $0.5 \times 10^6$, $0.25 \times 10^6$, $0.1 \times 10^6$, $0.05 \times 10^6$ and $0.025 \times 10^6$ in 100 μl volume followed by discarding blocking solution. The cells were activated by adding 100 μl of diluted mitogen mixture in 10% FBS RPMI 1640 to the plate (PHA-L, 5 μg/ml, PMA, 5 ng/ml). The ELISPOT plate was incubated in the $CO_2$ incubator for 24 hours. 200 μl of the cell suspension in wells was aspirated and plate was washed three times by soaking wells for 3-5 minutes for each washing. 100 μl of biotinylated anti mouse IFN-γ detection antibody was added to each well and then incubated for 2 hours at room temperature. The plate was emptied and washed three times with supplied buffer and then diluted streptavidin HRP conjugate was added to each well, and incubated for one hour at room temperature. The plate was washed 4 times with washing buffer I and then twice with washing buffer II. Substrate DAB was added to each well. Spot development was monitored for 30 minutes. The reaction was stopped by washing the wells with DI water and the plate was air-dried overnight at room temperature in the dark. The ELISPOT was read and analyzed by an ELISPOT scanner (ImmunoSpot, Cellular, Technology Ltd.)

Antibody targeted human tumor H23 mouse model imaging: The H23 human lung cancer cells were cultured in 10×10 cm dishes in RPMI 1640 medium with 10% FBS plus supplements. The cells were detached by using cold PBS and collected in 15 ml centrifuge tubes when tumor cells sub-confluent. The tumor cells were injected in athymic Nu/Nu mice at 1×10⁶/hind limb. The AF750 fluorescent dye was conjugated to purified 7D4 antibody. The conjugation method was following the protocol from Molecular probes. Briefly, dissolving the lyophilized powder in DMSO to form 10 mg/ml and then aliquot in small amount, and stored at −20 C. Whence antibody conjugation performance, 1M sodium bicarbonate (pH 9.0) was added into 2C6F3 antibody to form 0.1 M sodium bicarbonate in antibody solution (pH8.3) and then added AF750 to antibody solution. The ratio is Antibody: AF750=10:1 by amount and mixed well. The reaction rotated over two hours wrapped by an aluminum foil. The free dye was cleaned by a using a 3K size exclusion centrifugation column (Pall Corporation). Conjugated antibody was harvested. Concentration of labeled antibody and degree of labeling were tested according to the method from the company. Finally, the labeled antibody was adjusted to 50 µg/100 µl PBS then injected through tail vein once the tumor size reached to 0.5-0.8 cm, then irradiated with 3Gyx3 and 5Gyx1 and sham 0Gy. The mice were anesthetized for imaging every 24 hours by using an in vivo multi-spectral NIR system (Kodak imager) (Optical Radiology Laboratory).

Antigen identification targeted by monoclonal antibody: Cultured H23 cell was irradiated at 3Gyx3, 3Gyx1 and sham 0Gy. The cells were washed three times with warmed PBS at 37° C. and 10 ml of cold PBS was added to the dishes to detach for 5 minutes, the tumor cells were harvested into 50 ml centrifuge tubes. The cells were centrifuged at 1400 rpm for 8 minutes. The cell pellets were lysed by the freeze/thaw method 5 times in liquid nitrogen and 37° C. water bath with lysis buffer by supplement proteinase inhibitor cocktail. The cell lysate was centrifuged at 5000 rpm for 30 minutes and the supernatant was harvested as the source of cell lysate antigens. Protein concentration was determined and Western-blot was used for analysis of X-ray induced antigen recognized by the purified monoclonal antibodies as above. 10 micro-gram of cell lysate was loaded on the designated lanes and the proteins were separated by 10% gel then transferred to a nitrocellulose (NC) membrane at 4° C. overnight at low current. The NC membranes were washed three times in 0.1% Tween20 in PBS and then blocked with 5% NFDM plus 0.5% BSA in the same buffer. The purified monoclonal antibody was added to the membrane at the concentration of 5 µg/ml in 5% NFDM then incubated for one hour at RT. The NC membranes were then washed three times again and incubated with secondary antibody goat anti mouse IgG Fc conjugated to HRP at 1:4000 in 5% NFDM in 0.1% Tween 20 PBS for another 2 hours. Finally, ECL was added to the membranes after completed washing. The photographic films were developed for analysis protein bands.

Specific antigen affinity purification by IP and identification: The purified monoclonal antibody 7D4 was conjugated to cyanogens bromide-activated Sepharose 4B (Sigma). X-ray treated H23 cell lysates were prepared as above and applied to antibody conjugated beads individually (pre-conjugated to each column). Based off the cell lysate, various treatment groups of 0Gy, 3Gyx1, 3Gyx3 were mixed for conjugation at 4° C. for overnight. The columns were packed and washed with PBS and then eluted with a 0.1 M Na-citric elution buffer pH2.8 to collect the specific antigens captured by purified antibody. Western-blot assays were used to confirm the purified antigens from affinity column.

Antibody identified protein sequence: The specific protein bands detected through Western-blot by purified antibody were excised in a SDS-PAGE gel and sent to Vanderbilt University Mass-Spectrometry Research Center for proteomics analysis of the protein.

Purified protein identification and localization: IHC was used to confirm the binding on the treated tumor cells. Briefly, a commercial rabbit anti 14-3-3 epsilon antibody was used for this assay. X-ray treated H23 cells at 3Gyx3, 3Gyx1 or sham 0Gy cell smear on slides were prepared and performed as IHC above to compare with purified 7D4 produced in house. Normal mouse IgG or secondary antibody only was used for the controls.

Specific anti 14-3-3 epsilon antibody epitope mapping and sub-class identification: Human 14-3-3 Protein epsilon and its isoform SV whole amino acid sequences were obtained through UniProtKB/Swiss-Prot. The Taxonomic identifier 9606 (NCBI) organism is Homosapiens (Human), Gene name is YWHAE. Peptide designed from whole sequences of 14-3-3 protein epsilon and its isoform 14-3-3 protein epsilon SV. The designed peptides contain 18AA from N terminal to C terminal and had 2AA overlapped in each peptide. A total of 31 peptides synthesized by Sigma. The synthesized peptide was prepared in DMSO and then further diluted in PBS for coating an ELISA plate. 30 µg/ml and 10 µg/ml of peptides in PBS were coated on ELISA plates, 50 µL/well. The plates incubated overnight at 4° C., were washed with 0.1% Tween20 PBS and blocked with 3% BSA in same buffer for 1 hour. 50 µl dilution of purified anti 14-3-3 protein Epsilon antibody at the concentration of 5 µg/ml was added to each well, and incubated for 2 hours in a humid chamber in RT. A goat anti-mouse IgG Fc-gamma chain specific HRP conjugated secondary antibody was diluted at 1:4000 and added to each well followed by washing of the plates 5 times. After washing again, substrate ABTS was added to each well to monitor color change by reading at 405 nm in an ELISA reader (Bio-Tek Instrument Inc.). A mouse Ig isotyping kit was purchased from Southern Biotech (Birmingham Ala.) included IgG1, 2a, 2b, IgG3, IgM and kappa lambda chain for purified antibody isotype test.

Antibody binding site AA sequence: Hybridoma clone 7D4 was cultured in complete FBS medium with all supplements. The cells were harvested, counted and then frozen in 10% DMSO+90% FBS hybridoma frozen medium, 2×10⁶/vial. The vials were shipped to Genscript (Piscataway, N.J. USA) for antibody binding site sequence.

REFERENCES

1. Ghazal Hariri, Ying Zhang; Zhaozhong Han; Allie Fu; Martin Brechbiel; Noor Tantawy; Todd Peterson, Hallahan, Dennis. Radiation-guided P-selectin targeted tumor imaging in a lung tumor model. Annals of Biomedical Engineering. 36(5): 821-830. 2008
2. Wong J Y C, Chu D Z, Yamauchi D M, Williams L E, Liu A, Wilczynski S, Wu A M, Shively J E, Doroshow J H, Raubitschek A A. A phase I radioimmunotherapy trial evaluating 90yttrium-labeled anti-carcinoembryonic antigen (CEA) chimeric T84.66 in patients with metastatic CEA-producing malignancies. Clin Cancer Res. 2000 Oct. 6(10):3855-63.
3. Richman C M, Denardo S J, O'Donnell R T, Yuan A, Shen S, Goldstein D S, Tuscano J M, Wun T, Chew H K, Lara P N, Kukis D L, Natarajan A, Meares C F, Lamborn K R, DeNardo G L. High-dose radioimmunotherapy combined with fixed, low-dose paclitaxel in metastatic prostate and breast cancer by using a MUC-1 monoclonal antibody, m170, linked to indium-111/yttrium-90 via a cathepsin cleavable linker with cyclosporine to prevent human anti-mouse antibody. Clin Cancer Res. 2005 Aug. 15; 11(16):5920-7.
4. Hallahan D E, et al. Control of pharmacokinetics and pharmacodynamics of drug delivery by use of radiation. Am J. Clin Oncol 2001 b; 24:473-480
5. Clynes R A, Towers T L, Presta L G, Ravetch J V. Inhibitory Fc receptors modulate in vivo cytoxicity against tumor targets. Nat Med. 2000 April; 6(4):443-6.
6. Raymond L. Mernaugh, Heping Yan, Dong Chen, Jennifer Edl, Gregory Hanley, Ambra Pozzi, Roy Zent. Production and Characterization of Mouse Ureteric Bud cell-specificrat hybridoma antibody utilizing subtractive immunization and high-throughput screening. Jornal of Immunological Methods 306 (2005) 115-127.
7. Ning Y, Wang Y, Li Y, Hong Y, Peng D, Liu Y, Wang J, Hao W, Tian X, Wu F, Dong W, Wang L, Wu Q, Liu X, Gao J, He F, Qian X, Sun Q H, Li M. An alternative strategy for high throughput generation and characterization of monoclonal antibodies against human plasma proteins using fractionated native proteins as immunogens. Proteomics. 2006 January; 6(2):438-48.
8. Clynes R, Takechi Y, Moroi Y, Houghton A, Ravetch J V. Fc receptors are required in passive and active immunity to melanoma. Proc Natl Acad Sci USA. 1998 Jan. 20; 95(2):652-655
9. Desjarlais J R, Lazar G A, Zhukovsky E A, Chu S Y. Optimizing engagement of the immune system by anti-tumor antibodies: an engineer's perspective. Drug Discov Today. 2007 November; 12(21-22):898-910.
10. Zuo S, Xue Y, Tang S, Yao J, Du R, Yang P, Chen X. 14-3-3 epsilon dynamically interacts with key components of mitogen-activated protein kinase signal module for selective modulation of the TNF-alpha-induced time course-dependent NF-kappaB activity. J Proteome Res. 2010 Jul. 2; 9(7):3465-78.
11. Divgi C R, Bander N H, Scott A M, O'Donoghue J A, Sgouros G, Welt S, Finn R D, Morrissey F, Capitelli P, Williams J M, Deland D, Nakhre A, Oosterwijk E, Gulec S, Graham M C, Larson S M, Old L J. Phase I/II radioimmunotherapy trial with iodine-131-labeled monoclonal antibody G250 in metastatic renal cell carcinoma. Clin Cancer Res. 1998 November; 4(11): 2729-39.
12. Cai, Weibo, Yun Wu, Kai Chen, Qizhen Cao, David A. Tice, and Xiaoyuan Chen. In-vito and In-vivo characterization of 64Cu-labeled Abegrin™, a humanized monoclonal antibody against integrin AvB3. Cancer Res 2006; 66: (19). 9673.
13. Hallahan D E, Geng L, Cmelak A J, Chakravarthy Aft Martin W, Scarfone C, Gonzalez A. Targeting drug delivery to radiation-induced neoantigens in tumor microvasculature. J Control Release. 2001 Jul. 6; 74(1-3):183-91.
14. Oriente F, Andreozzi F, Romano C, Perruolo G, Perfetti A, Fiory F, Miele C, Beguinot F, Formisano P. Protein kinase C-alpha regulates insulin action and degradation by interacting with insulin receptor substrate-1 and 14-3-3 epsilon. J Biol Chem. 2005 Dec. 9; 280(49):40642-9. Epub 2005 Oct. 10.
15. Telles E, Hosing A S, Kundu S T, Venkatraman P, Dalal S N. A novel pocket in 14-3-3 epsilon is required to mediate specific complex formation with cdc25C and to inhibit cell cycle progression upon activation of checkpoint pathways. Exp Cell Res. 2009 May 1; 315(8):1448-57. Epub 2009 Jan. 31.
16. Lee E K, Lee Y S, Lee H, Choi C Y, Park S H. 14-3-3 epsilon protein increases matrix metalloproteinase-2 gene expression via p38 MAPK signaling in NIH3T3 fibroblast cells. Exp Mol Med. 2009 Jul. 31; 41(7):453-561.
17. Heidi major Sleister, A Gururaj Rao. Subtractive immunization: A tool for the generation of discriminatory antibodies to proteins of similar sequence. Journal of Immunological Methods. 261 (1-2) 213-220, March 2002.
18. Raymond L. Mernaugh, Heping Yan, Dong Chen, Jennifer Edl, Gregory Hanley, Ambra Pozzi, Roy Zent Production and Characterization of mouse ureteric bud cell-specific rat hybridoma antibodies utilizing subtractive immunization and high-throughput screening. Journal of Immunological Methods. 306 115-127, 2005.
19. Mariana Ferreira Leal, Danielle Queiroz Calcagno, Sâmia Demachki, Paulo Pimentel Assumpção, Roger Chammas, Rommel Rodríguez Burbano, and Marília de Arruda Cardoso Smith Clinical implication of 14-3-3 epsilon expression in gastric cancer. World J. Gastroenterology. 18(13)1531-1537, 2012.
20. Qi W1, Liu X, Qiao D, Martinez J D. Isoform-specific expression of 14-3-3 proteins in human lung cancer tissues. Int. J. cancer. 113(3) 359-363, 2005.
21. Zhihui Wang, Jahn M. Nesland, Zhenhe Suo, Claes G. Trope, Ruth Holm. The Prognostic Value of 14-3-3 Isoforms in Vulvar Squamous Cell Carcinoma Cases: 14-3-3β and ε Are Independent Prognostic Factors for These Tumors. PloS ONE Volume 6 Issue 9, September 2011.

What is claimed is:

1. An isolated antibody, wherein the antibody specifically binds 14-3-3 epsilon and the heavy chain comprises the amino acid-sequences of SEQ ID NOs: 8, 9, and 10, and the light chain comprises the amino acid-sequences of SEQ ID NOs: 5, 6, and 7.

2. The isolated antibody of claim 1, wherein the antibody is encoded by a nucleic acid sequence comprising a nucleic acid sequence selected from the group consisting of SEQ ID NO:1 and SEQ ID NO:2.

3. The isolated antibody of claim 1, wherein the antibody specifically binds to an epitope selected from the group consisting of SEQ ID NO:13, SEQ ID NO:14 and SEQ ID NO:15.

4. The isolated antibody of claim 1, wherein the antibody is selected from the group consisting of a single-chain antibody, an antibody fragment, a chimeric antibody, or a humanized antibody.

5. The isolated antibody of claim 1, wherein the antibody is conjugated directly or indirectly to a payload selected from the group consisting of a detectable label, a therapeutic agent, or a combination thereof.

6. The isolated antibody of claim 1, wherein the antibody is conjugated directly or indirectly to a nanoparticle or a liposome.

7. The isolated antibody of claim 5, wherein the detectable label and/or therapeutic agent is a radionuclide.

8. A method of detecting a tumor in a subject, the method comprising:
 a) exposing a target area of the subject where the presence of a tumor is suspected to ionizing radiation;
 b) administering to the subject a composition to detect the presence of 14-3-3 epsilon in the target area, wherein the composition comprises one or more targeting antibodies of claim 1, wherein each targeting antibody specifically binds to 14-3-3 epsilon exposed on an irradiated cell and is conjugated to a detectable label; and
 c) detecting the detectable label to detect the presence of 14-3-3 epsilon, wherein the presence of 14-3-3 epsilon indicates the presence of a tumor in the target area of the subject.

9. The method of claim 8, wherein the exposing comprises exposing the tumor to at least about 2 Gy ionizing radiation.

10. The method of claim 8, wherein the administering comprises administering the antibody 0 hours to about 24 hours following radiation exposure.

11. The method of claim 8, wherein the detectable label is a radionuclide.

12. The method of claim 11, wherein the detecting comprises detecting the radionuclide label using positron emission tomography, single photon emission computed tomography, gamma camera imaging, or rectilinear scanning.

13. The method of claim 8, wherein the tumor is a lung carcinoma.

14. A method of enhancing radiotherapy in a subject, the method comprising administering to the subject a pharmacologically effective amount of the isolated anti-14-3-3 epsilon antibody of claim 1, wherein the isolated anti-14-3-3 epsilon antibody is conjugated to a therapeutic agent, such that radiotherapy is enhanced.

15. The method of claim 14, wherein the subject has cancer.

16. The method of claim 15, wherein the cancer is lung carcinoma.

17. The method of claim 14, wherein the administering comprises administering the antibody subsequent to radiation exposure.

* * * * *

SEQUENCE LISTING

<160> NUMBER OF SEQ ID NOS: 17

<210> SEQ ID NO 1
<211> LENGTH: 339
<212> TYPE: DNA
<213> ORGANISM: Artificial Sequence
<220> FEATURE:
<223> OTHER INFORMATION: SYNTHESIZED

<400> SEQUENCE: 1

```
gacattgtga tgacacagtc tccatcctcc ctggctatgt cagtaggaca gaaggtcact      60
atgagctgca agtccagtca gagcctttta aatagtagca atcaaaagaa ctatttggcc     120
tggtaccagc agaaaccagg acagtctcct aaacttctgg tatactttgc atccactagg     180
```

```
gaatctgggg tccctgatcg cttcataggc agtggatctg ggacagattt cactcttacc    240
atcagcagtg tgcaggctga agacctggca gattacttct gtcagcaaca ttatagcact    300
ccgctcacgt tcggtgctgg gaccaagctg agctgaaa                            339
```

<210> SEQ ID NO 2
<211> LENGTH: 357
<212> TYPE: DNA
<213> ORGANISM: Artificial Sequence
<220> FEATURE:
<223> OTHER INFORMATION: SYNTHESIZED

<400> SEQUENCE: 2

```
caggttcagc tgcagcagtc tggagctgag ctgatgaagc ctggggcctc agtgaagata     60
tcctgcaagg ctactggcta cacattcagt agctactgga tagagtgggt aaagcagagg    120
cctggacatg gccttgagtg gattggagag atttttacctg aagtggtag tactaactac    180 aatgagaagt tcaagggcaa ggccacattc actgcagata catcctccaa cacagcctac    240
atgcaactca gcagcctgac atctgaggac tctgccgtct attactgtgc aagatcggta    300
tggttacgac gtgattttgc ttactggggc caagggactc tggtcactgt ctctgca       357
```

<210> SEQ ID NO 3
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 3

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 4
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 4

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile

```
                35                  40                  45
Gly Glu Ile Leu Pro Gly Ser Gly Ser Thr Asn Tyr Asn Glu Lys Phe
        50                  55                  60
Lys Gly Lys Ala Thr Phe Thr Ala Asp Thr Ser Ser Asn Thr Ala Tyr
 65                  70                  75                  80
Met Gln Leu Ser Ser Leu Thr Ser Glu Asp Ser Ala Val Tyr Tyr Cys
                85                  90                  95
Ala Arg Ser Val Trp Leu Arg Arg Asp Phe Ala Tyr Trp Gly Gln Gly
                100                 105                 110
Thr Leu Val Thr Val Ser Ala
        115

<210> SEQ ID NO 5
<211> LENGTH: 17
<212> TYPE: PRT
<213> ORGANISM: Artificial Sequence
<220> FEATURE:
<223> OTHER INFORMATION: SYTHENSIZED

<400> SEQUENCE: 5

Lys Ser Ser Gln Ser Leu Leu Asn Ser Ser Asn Gln Lys Asn Tyr Leu
 1               5                  10                  15

Ala

<210> SEQ ID NO 6
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 6

Phe Ala Ser Thr Arg Glu Ser
 1               5

<210> SEQ ID NO 7
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 7

Gln Gln His Tyr Ser Thr Pro Leu Thr
 1               5

<210> SEQ ID NO 8
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 8

Gly Tyr Thr Phe Ser Ser Tyr Trp Ile Glu
 1               5                  10

<210> SEQ ID NO 9
<211> LENGTH: 17
<212> TYPE: PRT
<213> ORGANISM: Artificial Sequence
<220> FEATURE:
<223> OTHER INFORMATION: SYNTHESIZED
```

<400> SEQUENCE: 9

Glu Ile Leu Pro Gly Ser Gly Ser Thr Asn Tyr Asn Glu Lys Phe Lys
1               5                   10                  15

Gly

<210> SEQ ID NO 10
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 10

Ser Val Trp Leu Arg Arg Asp Phe Ala Tyr
1               5                   10

<210> SEQ ID NO 11
<211> LENGTH: 255
<212> TYPE: PRT
<213> ORGANISM: Homo sapiens

<400> SEQUENCE: 11

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
                20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 12
<211> LENGTH: 233

```
<212> TYPE: PRT
<213> ORGANISM: Homo sapiens

<400> SEQUENCE: 12

Met Val Glu Ser Met Lys Lys Val Ala Gly Met Asp Val Glu Leu Thr
1               5                   10                  15

Val Glu Glu Arg Asn Leu Leu Ser Val Ala Tyr Lys Asn Val Ile Gly
            20                  25                  30

Ala Arg Arg Ala Ser Trp Arg Ile Ile Ser Ser Ile Glu Gln Lys Glu
        35                  40                  45

Glu Asn Lys Gly Gly Glu Asp Lys Leu Lys Met Ile Arg Glu Tyr Arg
    50                  55                  60

Gln Met Val Glu Thr Glu Leu Lys Leu Ile Cys Cys Asp Ile Leu Asp
65                  70                  75                  80

Val Leu Asp Lys His Leu Ile Pro Ala Ala Asn Thr Gly Glu Ser Lys
                85                  90                  95

Val Phe Tyr Tyr Lys Met Lys Gly Asp Tyr His Arg Tyr Leu Ala Glu
            100                 105                 110

Phe Ala Thr Gly Asn Asp Arg Lys Glu Ala Ala Glu Asn Ser Leu Val
        115                 120                 125

Ala Tyr Lys Ala Ala Ser Asp Ile Ala Met Thr Glu Leu Pro Pro Thr
    130                 135                 140

His Pro Ile Arg Leu Gly Leu Ala Leu Asn Phe Ser Val Phe Tyr Tyr
145                 150                 155                 160

Glu Ile Leu Asn Ser Pro Asp Arg Ala Cys Arg Leu Ala Lys Ala Ala
                165                 170                 175

Phe Asp Asp Ala Ile Ala Glu Leu Asp Thr Leu Ser Glu Glu Ser Tyr
            180                 185                 190

Lys Asp Ser Thr Leu Ile Met Gln Leu Leu Arg Asp Asn Leu Thr Leu
        195                 200                 205

Trp Thr Ser Asp Met Gln Gly Asp Gly Glu Glu Gln Asn Lys Glu Ala
    210                 215                 220

Leu Gln Asp Val Glu Asp Glu Asn Gln
225                 230

<210> SEQ ID NO 13
<211> LENGTH: 18
<212> TYPE: PRT
<213> ORGANISM: Homo sapiens

<400> SEQUENCE: 13

Phe Ser Val Phe Tyr Tyr Glu Ile Leu Asn Ser Pro Asp Arg Ala Cys
1               5                   10                  15

Arg Leu

<210> SEQ ID NO 14
<211> LENGTH: 18
<212> TYPE: PRT
<213> ORGANISM: Homo sapiens

<400> SEQUENCE: 14

His Pro Ile Arg Leu Gly Leu Ala Leu Asn Phe Ser Val Phe Tyr Tyr
1               5                   10                  15

Glu Ile

<210> SEQ ID NO 15
<211> LENGTH: 10
```

```
<212> TYPE: PRT
<213> ORGANISM: Homo sapiens

<400> SEQUENCE: 15

Phe Ser Val Phe Tyr Tyr Glu Ile Leu Asn
1               5                   10

<210> SEQ ID NO 16
<211> LENGTH: 138
<212> TYPE: PRT
<213> ORGANISM: Artificial Sequence
<220> FEATURE:
<223> OTHER INFORMATION: SYNTHESIZED

<400> SEQUENCE: 16

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Ser Val Trp Leu Arg Arg Asp Phe Ala Tyr Trp
        115                 120                 125

Gly Gln Gly Thr Leu Val Thr Val Ser Ala
    130                 135

<210> SEQ ID NO 17
<211> LENGTH: 133
<212> TYPE: PRT
<213> ORGANISM: Artificial Sequence
<220> FEATURE:
<223> OTHER INFORMATION: SYNTHESIZED

<400> SEQUENCE: 17

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Leu Thr Phe Gly Ala Gly Thr
        115                 120                 125
```

```
Lys Leu Glu Leu Lys
    130
```